United States Patent [19]

Watson et al.

[11] Patent Number: 4,818,694

[45] **Date of Patent: * Apr. 4, 1989**

[54] PRODUCTION OF HERPES SIMPLEX VIRAL PROTEIN

[75] Inventors: Roger J. Watson; John W. Weis, both of Minneapolis; Lynn W. Enquist, Excelsior, all of Minn.

[73] Assignee: American Cyanamid Company, Stamford, Conn.

[ * ] Notice: The portion of the term of this patent subsequent to Apr. 4, 2006 has been disclaimed.

[21] Appl. No.: 400,028

[22] Filed: Jul. 20, 1982

[51] Int. Cl.[4] ........................ C12P 21/00; C12P 21/02; C12P 21/04; C12N 15/00; C12N 5/00; C12N 1/00; C12N 1/20; C12N 1/16; C12N 1/18; C07H 21/04

[52] U.S. Cl. ........................................ 435/68; 435/70; 435/71; 435/172.1; 435/172.3; 435/240.1; 435/240.2; 435/243; 435/252.33; 435/255; 435/256; 435/320; 536/27; 935/12; 935/28; 935/29; 935/52; 935/66; 935/69; 935/70; 935/72; 935/73

[58] Field of Search ..................... 435/68, 70, 91, 172, 435/253, 317, 317.1, 320, 255, 256, 240.1, 240.2, 71, 172.3, 172.1, 243; 536/27; 935/11, 12, 52, 66–75, 28, 29, 31, 32

[56] References Cited

U.S. PATENT DOCUMENTS

| | | | |
|---|---|---|---|
| 4,237,224 | 12/1980 | Cohen et al. | 435/68 |
| 4,332,892 | 6/1982 | Ptashne et al. | 435/70 |
| 4,338,397 | 7/1982 | Gilbert et al. | 435/70 |
| 4,343,832 | 8/1982 | Goeddel et al. | 435/70 |
| 4,346,629 | 9/1982 | Carey et al. | 435/172 |
| 4,366,246 | 12/1982 | Riggs | 435/172 |
| 4,374,127 | 2/1983 | Larson et al. | 424/89 |
| 4,419,446 | 12/1983 | Howley et al. | 435/91 |
| 4,618,578 | 10/1986 | Burke et al. | 435/68 |
| 4,709,011 | 11/1987 | Cohen et al. | 530/324 |

FOREIGN PATENT DOCUMENTS

| | | | |
|---|---|---|---|
| 17452/83 | 2/1984 | Australia | 435/172.3 |

OTHER PUBLICATIONS

Maxam et al.: Proc. Natl. Acad. Sci. USA 74, 560 (1977).
Roberts et al., "A general method for maximizing the expression of a cloned gene", Proc. Natl. Acad. Sci. USA 76: 760 (1979).
Hitzeman et al., "Expression of a human gene for interferon in yeast", Nature 293: 717 (1981).
Post, et al.,–Proceedings National Academy of Science, U.S.A. vol. 77, No. 7, pp. 4201–4205, Jul. 1980.
Enquist et al., 1979, Science 203: 541–544.
Docherty et al., 1981, J. Virol. 40: 126–132.
Galloway et al., 1982, J. Virol. 42(2): 530–537.
Randall et al., 1980, J. Gen. Virol 48: 297–310.
Eisenberg et al., 1980, J. Virol 35: 428–435.
Cohen et al., 1980, J. Virol 34: 521–531.
Cohen et al., 1978, J: Virol. 27: 172–181.
Eisenberg et al., 1979, J. Virol. 31: 608–620.
Eisenberg et al., 1982, J. Virol. 41: 1099–1104.
Cohen et al., 1980, J. Virol. 36: 429–439.
Ponce de Leon et al., 1973, J. Virol. 12: 766–774.
Cohen et al., 1972, J. Virol. 10: 1021–1030.
Pereira et al., 1982, Infect. Immun. 35: 363–367.
Dix et al., 1981, Infect. Immun. 34: 192–199.
Periera et al., 1980, Infect. Immun. 29: 724–732.
Pizer et al., 1980, J. Virol. 34: 142–153.

(List continued on next page.)

*Primary Examiner*—James Martinell
*Attorney, Agent, or Firm*—Robert P. Raymond

[57] ABSTRACT

Methods and composition are provided for the cloning and expression of a Herpes Simplex Virus (HSV) glycoprotein (gD) gene in single-cell host organisms. Also described are methods for culturing these novel single-cell organisms to produce the HSV-gene product. The HSV gD-related polypeptide produced by the recombinant DNA techniques described herein may be formulated for use as an immunogen in a vaccine to protect against HSV-1 and HSV-2 infection.

61 Claims, 14 Drawing Sheets

OTHER PUBLICATIONS

Zhidkova et al., Chem. Abstracts 100:80679Z (1984).
Berman et al., *Trends in Biochemistry,* vol. 3, pp. 51–53 (1985).
Weis et al., 1983, Nature 302: 72–74.
Watson et al., 1982, Science 218: 381–383.
Lee et al., 1982, Proc. Natl. Acad. Sci. USA, 79: 6612–6616.
Itakura et al., 1977, Science 198: 1056.
Villa-Komaroff et al., 1978, Proc. Natl. Acad. Sci. USA 75: 3727.
Seeberg et al., 1978, Nature 276: 795.
Mercereau-Puijalon et al., 1978, Nature 275: 505.
Fraser et al., 1978, Proc. Natl. Acad. Sci. USA 75: 5936.
Guarente et al., 1980, Cell 20: 543.
Norrild, Current Topics in Microbiol. and Immunol. 19: 67.
Ruyechan et al., 1979, J. Virol. 29: 677.
Lee et al., 1982, J. Virol. 43: 41.
Umene et al., 1981, Gene 13: 251.
Watson et al., 1981, J. Virol 37: 431.
Showalter et al., 1981, Infection and Immunity 34: 684.
Hampar et al., U.S. Patent Applic. No. 06/181,954, National Technical Information Service.

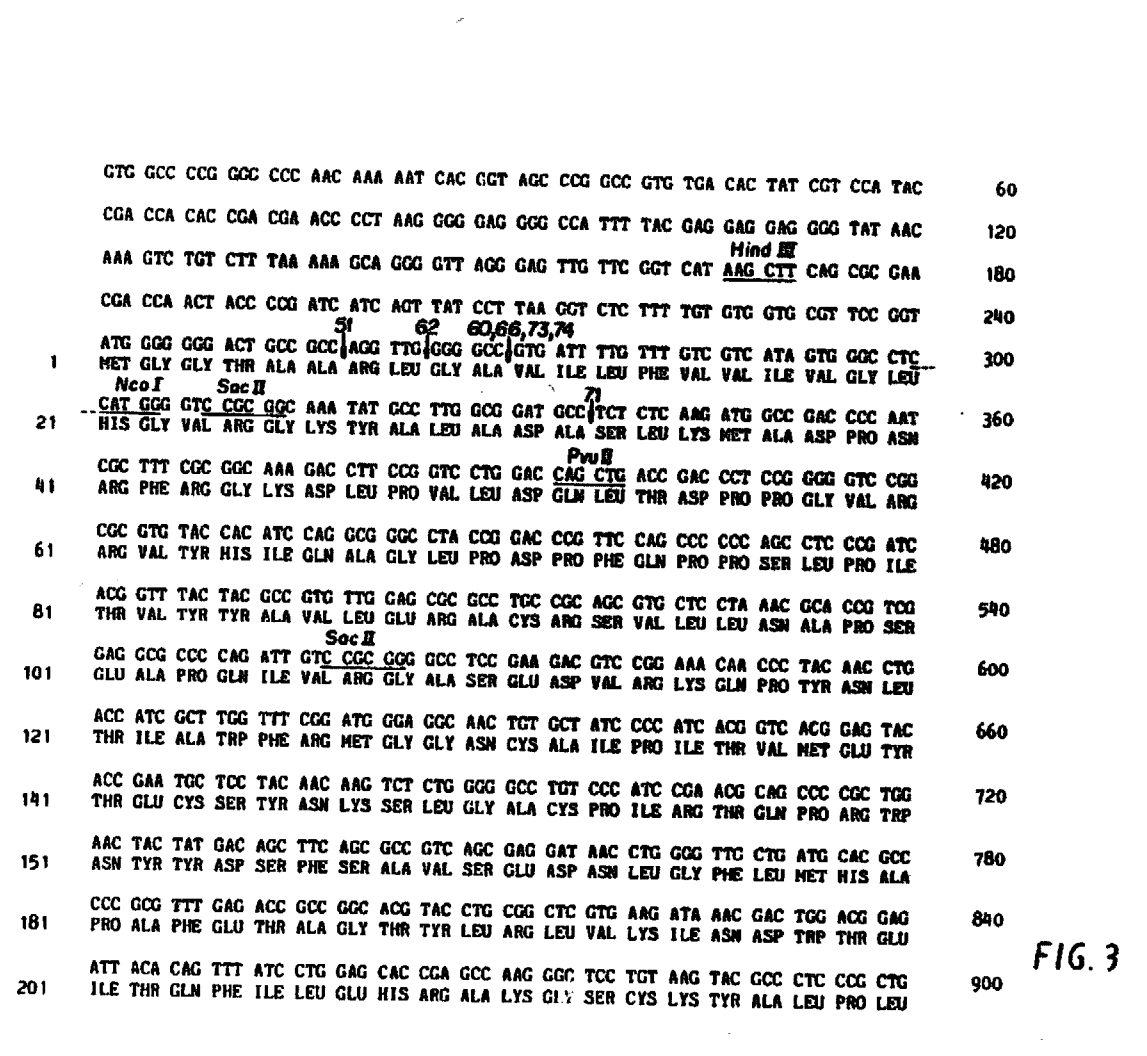

```
                                                                                   
          GTG GCC CCG GGC CCC AAC AAA AAT CAC GGT AGC CCG GCC GTG TGA CAC TAT CGT CCA TAC      60
          CGA CCA CAC CGA CGA ACC CCT AAG GGG GAG GGG CCA TTT TAC GAG GAG GAG GGG TAT AAC     120
                                                                   Hind III
          AAA GTC TGT CTT TAA AAA GCA GGG GTT AGG GAG TTG TTC GGT CAT AAG CTT CAG CGC GAA     180
          CGA CCA ACT ACC CCG ATC ATC AGT TAT CCT TAA GGT CTC TTT TGT GTG GTG CGT TCC GGT     240
                                  51      62  60,66,73,74
          ATG GGG GGG ACT GCC GCC|AGG TTG|GGG GCC|GTG ATT TTG TTT GTC GTC ATA GTG GGC CTC     300
  1       MET GLY GLY THR ALA ALA ARG LEU GLY ALA VAL ILE LEU PHE VAL VAL ILE VAL GLY LEU
           NcoI    SacII                      71
          CAT GGG GTC CGC GGC AAA TAT GCC TTG GCG GAT GCC|TCT CTC AAG ATG GCC GAC CCC AAT     360
 21       HIS GLY VAL ARG GLY LYS TYR ALA LEU ALA ASP ALA SER LEU LYS MET ALA ASP PRO ASN
                                                  PvuII
          CGC TTT CGC GGC AAA GAC CTT CCG GTC CTG GAC CAG CTG ACC GAC CCT CCG GGG GTC CGG     420
 41       ARG PHE ARG GLY LYS ASP LEU PRO VAL LEU ASP GLN LEU THR ASP PRO PRO GLY VAL ARG
          CGC GTG TAC CAC ATC CAG GCG GGC CTA CCG GAC CCG TTC CAG CCC CCC AGC CTC CCG ATC     480
 61       ARG VAL TYR HIS ILE GLN ALA GLY LEU PRO ASP PRO PHE GLN PRO PRO SER LEU PRO ILE
          ACG GTT TAC TAC GCC GTG TTG GAG CGC GCC TGC CGC AGC GTG CTC CTA AAC GCA CCG TCG     540
 81       THR VAL TYR TYR ALA VAL LEU GLU ARG ALA CYS ARG SER VAL LEU LEU ASN ALA PRO SER
                                  SacII
          GAG GCG CCC CAG ATT GTC CGC GGG GCC TCC GAA GAC GTC CGG AAA CAA CCC TAC AAC CTG     600
101       GLU ALA PRO GLN ILE VAL ARG GLY ALA SER GLU ASP VAL ARG LYS GLN PRO TYR ASN LEU
          ACC ATC GCT TGG TTT CGG ATG GGA GGC AAC TGT GCT ATC CCC ATC ACG GTC ACG GAG TAC     660
121       THR ILE ALA TRP PHE ARG MET GLY GLY ASN CYS ALA ILE PRO ILE THR VAL MET GLU TYR
          ACC GAA TGC TCC TAC AAC AAG TCT CTG GGG GCC TGT CCC ATC CGA ACG CAG CCC CGC TGG     720
141       THR GLU CYS SER TYR ASN LYS SER LEU GLY ALA CYS PRO ILE ARG THR GLN PRO ARG TRP
          AAC TAC TAT GAC AGC TTC AGC GCC GTC AGC GAG GAT AAC CTG GGG TTC CTG ATG CAC GCC     780
151       ASN TYR TYR ASP SER PHE SER ALA VAL SER GLU ASP ASN LEU GLY PHE LEU MET HIS ALA
          CCC GCG TTT GAG ACC GCC GGC ACG TAC CTG CGG CTC GTG AAG ATA AAC GAC TGG ACG GAG     840
181       PRO ALA PHE GLU THR ALA GLY THR TYR LEU ARG LEU VAL LYS ILE ASN ASP TRP THR GLU
          ATT ACA CAG TTT ATC CTG GAG CAC CGA GCC AAG GGC TCC TGT AAG TAC GCC CTC CCG CTG     900
201       ILE THR GLN PHE ILE LEU GLU HIS ARG ALA LYS GLY SER CYS LYS TYR ALA LEU PRO LEU
```

FIG. 3

```
     CGC ATC CCC CCG TCA GCC TGC CTC TCC CCC CAG GCC TAC CAG CAG GGG GTG ACG GTG GAC    960
221  ARG ILE PRO PRO SER ALA CYS LEU SER PRO GLN ALA TYR GLN GLN GLY VAL THR VAL ASP

     AGC ATC GGG ATG CTG CCC CGC TTC ATC CCC GAG AAC CAG CGC ACC GTC GCC GTA TAC AGC   1020
241  SER ILE GLY MET LEU PRO ARG PHE ILE PRO GLU ASN GLN ARG THR VAL ALA VAL TYR SER

     TTG AAG ATC GCC GGG TGG CAC GGG CCC AAG GCC CCA TAC ACG AGC ACC CTG CTG CCC CCG   1080
261  LEU LYS ILE ALA GLY TRP HIS GLY PRO LYS ALA PRO TYR THR SER THR LEU LEU PRO PRO

     GAG CTG TCC GAG ACC CCC AAC GCC ACG CAG CCA GAA CTC GCC CCG GAA GAC CCC GAG GAT   1140
281  GLU LEU SER GLU THR PRO ASN ALA THR GLN PRO GLU LEU ALA PRO GLU ASP PRO GLU ASP

     TCG GCC CTC TTG GAG GAC CCC GTG GGG ACG GTG GCG CCG CAA ATC CCA CCA AAC TGG CAC   1200
301  SER ALA LEU LEU GLU ASP PRO VAL GLY THR VAL ALA PRO GLN ILE PRO PRO ASN TRP HIS

     ATC CCG TCG ATC CAG GAC GCC GCG ACG CCT TAC CAT CCC CCG GCC ACC CCG AAC AAC ATG   1260
321  ILE PRO SER ILE GLN ASP ALA ALA THR PRO TYR HIS PRO PRO ALA THR PRO ASN ASN MET

     GGC CTG ATC GCC GGC GCG GTG GGC GGC AGT CTC CTG GCA GCC CTG GTC ATT TGC GGA ATT   1320
341  GLY LEU ILE ALA GLY ALA VAL GLY GLY SER LEU LEU ALA ALA LEU VAL ILE CYS GLY ILE

     GTG TAC TGG ATG CAC CGC CGC ACT CGG AAA GCC CCA AAG CGC ATA CGC CTC CCC CAC ATC   1380
361  VAL TYR TRP MET HIS ARG ARG THR ARG LYS ALA PRO LYS ARG ILE ARG LEU PRO HIS ILE

     CGG GAA GAC GAC CAG CCG TCC TCG CAC CAG CCC TTG TTT TAC TAG ATA CCC CCC CTT AAT   1440
381  ARG GLU ASP ASP GLN PRO SER SER HIS GLN PRO LEU PHE TYR ***

     GGG TGC GGG GGG GTC AGG TCT GCG GGG TTG GGA TGG GAC CTT AAC TCC ATA TAA AGC GAG   1500

     TCT GGA AGG GGG GAA AGG CGG ACA GTC GAT AAG TCG GTA GCG GGG GAC GCG CAC CTG TTC   1560
                                      NruI
     CGC CTG TCG CAC CCA CAG CTT TTT CGC GAA CCG TCC CGT TTT CGG GAT                   1608
```

```
    CRO
ATG GAA CAA CGC ATA ACC
MET GLU GLN ARG ILE THR

CTG AAA GAT TAT GCA ATG
LEU LYS ASP TYR ALA MET

CGC TTT GGG CAA ACC AAG
ARG PHE GLY GLN THR LYS

ACA GCT AAA GAT CTG CCC
THR ALA LYS ASP LEU PRO

gD
CTG ACC GAC CCT.....
LEU THR ASP PRO.....
```

| ANTISERA | NONE | | PRE-IMMUNE | | ANTI-HSV | |
|---|---|---|---|---|---|---|
| IPTG | − | + | − | + | − | + |
| | 1 | 2 | 3 | 4 | 5 | 6 |

92 —

68 —

43 —  　　　　　　　　　　　— ←— gD related protein

30 —

PRODUCTION OF HERPES SIMPLEX VIRAL PROTEIN

TABLE OF CONTENTS

1. Field of the Invention
2. Background of the Invention
  2.1 Recombinant DNA Technology and Gene Expression
  2.2 Herpes Viruses
3. Summary of the Invention
4. Description of the Figures
5. Description of the Invention
  5.1 Identification and Isolation of HSV Glycoprotein Genes
  5.2 Insertion of the HSV Glycoprotein Gene into a Cloning Expression Vector
  5.3 Preparation of Fusion Proteins
  5.4 Identification of the Gene Product
  5.5 Purification of the Gene Product
  5.6 Formulation of a Vaccine
6. Example
  6.1 General Procedures Used for Preparation of the Plasmids
    6.11 Plasmid DNA Isolation
    6.1.2 Conditions for Restriction Enzyme Digestions
    6.1.3 Restriction Enzyme Buffers
    6.1.4 Modification of DNA
    6.1.5 Gel Purification of DNA Fragments
    6.1.6 DNA Ligation
  6.2 Localization and Isolation of the gD Gene
    6.2.1 Recombinant DNA Plasmids Containing Defined Portions of the Us Region of HSV-1
    6.2.2 Localization of gD Specific mRNA Coding Sequence
    6.2.3 Characterization of the gD mRNA
  6.3 Cloning and Expression of the gD Gene
    6.3.1 The Expression Vector pJS413
    6.3.2 Insertion of the gD Gene into pJS413
    6.3.3 Identification of Transformants that Express the gD Gene
  6.4 Preparation of pEH4-2 which Directs the Production of a cro/gD/B-Galactosidase Fusion Protein
    6.4.1 Analysis of the pEH4-2 Fusion Protein
  6.5 Reconstruction of the gD Gene

1. FIELD OF THE INVENTION

This invention is directed to a process for the production of proteins related to any of the Herpes Simplex Virus (HSV) glycoproteins, and to processes and compositions for making and using novel DNA sequences, plasmids and microorganisms (both eucaryotic and procaryotic) to produce such proteins.

The present invention utilizes recombinant DNA techniques to insert a DNA sequence coding for glycoprotein D (gD), or a portion thereof, into a DNA vector, such as viral DNA, plasmid DNA or bacteriophage DNA, such that the vector is capable of replicating and directing expression of the gD gene in a bacterial host or other single cell system. The resulting recombinant DNA molecule is introduced into host cells and thereby enables production of gD, or a portion or molecular variant thereof, by the host cells. The protein produced is then isolated, purified and modified for use as an immunogen in a vaccine against infection of both HSV type 1 (HSV-1) and type 2 (HSV-2).

2. BACKGROUND OF THE INVENTION

2.1 RECOMBINANT DNA TECHNOLOGY AND GENE EXPRESSION

Recombinant DNA technology involves insertion of specific DNA sequences into a DNA vehicle (vector) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. In recent years several general methods have been developed which enable construction of recombinant DNA molecules. For example, U.S. Pat. No. 4,237,224 to Cohen and Boyer describes production of such recombinant plasmids using restriction enzymes and methods known as ligation. These recombinant plasmids are then introduced and replicated in unicellular organisms by means of transformation. Because of the general applicability of the techniques described therein, U.S. Pat. No. 4,237,224 is hereby incorporated by reference into the present specification.

Another method for introducing recombinant DNA molecules into unicellular organisms is described by Collins and Hohn in U.S. Pat. No. 4,304,863 which is also incorporated herein by reference. This method utilizes a packaging/transduction system with bacteriophage vectors.

Regardless of the method used for construction, the recombinant DNA molecule must be compatible with the host cell, i.e., capable of autonomous replication in the host cell. The recombinant DNA molecule should also have a marker function which allows the selection of host cells so transformed by the recombinant DNA molecule. In addition, if all of the proper replication, transcription and translation signals are correctly arranged on the plasmid, the foreign gene will be properly expressed in the transformed cells and their progeny.

As is characteristic of all viruses which infect eucaryotic cells, Herpes Simplex Virus requires a eucaryotic host cell system in which to replicate its genome, express its viral genes and generate its progeny. The signals and control elements for DNA replication, gene expression and virus assembly in eucaryotes differ from those of procaryotes. This is of critical importance when attempts are made to express in procaryotic host cells a gene which is naturally expressed only in eucaryotic cells.

These different genetic signals and processing events control many levels of gene expression, for instance, DNA transcription and messenger RNA translation. Transcription of DNA is dependent upon the presence of a promoter which is a DNA sequence that directs the binding of RNA polymerase and thereby promotes transcription. The DNA sequences of eucaryotic promoters differ from those of procaryotic promoters. Furthermore, eucaryotic promoters and accompanying genetic signals may not be recognized in or may not function in a procaryotic system.

Similarly, translation of messenger RNA (mRNA) in procaryotes depends upon the presence of the proper procaryotic signals which differ from those of eucaryotes. Efficient translation of mRNA in procaryotes requires a ribosome binding site called the Shine Dalgarno (SD) sequence on the mRNA. This sequence is a short nucleotide sequence of mRNA that is located before the start codon (AUG) which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, 1979, Methods in Enzymology 68: 473.

Many factors complicate the expression of eucaryotic genes in procaryotes even after the proper signals are inserted and appropriately positioned. A clear understanding of the nature of these factors and the mechanisms by which they operate is presently lacking. One such factor is the presence of an active proteolytic system in *E. coli* and other bacteria. This protein-degrading system appears to selectively destroy "abnormal" or foreign proteins such as eucaryotic proteins. A tremendous utility, therefore, would be afforded by the development of a means to protect eucaryotic proteins expressed in bacteria from proteolytic degradation. One strategy is to construct hybrid genes in which the eucaryotic sequence is ligated in phase (i.e., in the correct reading frame) with a procaryotic gene resulting in a fusion protein product (a protein that is a hybrid of procaryotic and foreign or eucaryotic amino acid sequences)

Construction of hybrid genes was the approach used in the molecular cloning of genes encoding a number of eucaryotic proteins, such as somatostatin (Itakura et al., 1977, Science 198: 1056), rat proinsulin (Villa-Komaroff et al., 1978, Proc. Natl. Acad. Sci., U.S.A. 75: 3727), growth hormone (Seeberg et al., 1978, Nature 276: 795), and ovalbumin-like protein (Mercereau-Puijalon et al., 1978, Nature 275: 505). Additionally, procaryotic promoters have been ligated to such fusion gene sequences in the case of ovalbumin (Fraser et al., 1978, Proc. Natl. Acad. Sci., U.S.A. 75: 5936) and B-globin (Guarente et al., 1980, Cell 20: 543). The Guarente et al. system involves inserting the lac promoter, including the SD sequence, at varying distances in front of the ATG of the fusion gene. Although the molecular cloning and expression of several eucaryotic genes has been accomplished, this has not heretofore been done for the gD gene. Nor is the state of the art such that expression of foreign or eucaryotic genes in procaryotic host cells may be routinely performed.

2.2 HERPES VIRUSES

Herpes viruses are eucaryotic viruses which contain a linear, double-stranded DNA genome which ranges in size from $80\times10^6$ to $150\times10^6$ daltons. In addition each virion has an icosahedral nucleocapsid and a membrane envelope which is formed by removal from the host cellular lipid bilayer during maturation and budding. The viral envelope is a lipid bilayer that contains a number of viral specific proteins which, although partially embedded in the membrane, protrude outward from the membrane envelope. During primary infection the membrane envelope is required for the efficient penetration of the viral particle into the cell. Antibodies which specifically bind to the viral proteins on the outside of the lipid bilayer are capable of neutralizing viral infectivity. Those viral proteins which are most essential to the entry of the virus into the cell are glycoproteins (protein molecules with sugar molecules associated therewith). Herpes Simplex Virus type 1 (HSV-1) and type 2 (HSV-2) each produce at least four different glycoproteins which are antigenically distinct from one another. Certain of these proteins from HSV-1 and HSV-2 share common epitopes (i.e., antigenic sites or antibody binding sites). An example of such a protein is a 49,000–58,000 dalton glycoprotein designated gD. Polyvalent antiserum against HSV-1 gD is capable of neutralizing both HSV-1 and HSV-2 infections (Norrild, 1979, Current Topics in Microbiol. and Immunol. 19: 67).

3. SUMMARY OF THE INVENTION

Methods and compositions are provided for the cloning and expression of an HSV glycoprotein gene in single-cell host organisms. Also described are methods for culturing these novel single-cell organisms to produce the HSV gene product and methods for the purification of the gene product. The gD-related protein produced by the recombinant DNA techniques described herein may be formulated for use as an immunogen in a vaccine to protect against HSV-1 and HSV-2 infection.

The HSV-1 gD gene (isolated from HSV-1 Patton Strain) was identified in the viral genome by intertypic recombinational analysis and mRNA mapping. Once localized on a specific segment of DNA, the nucleotide sequence of the gene was determined and the amino acid sequence of the gD protein was predicted.

The isolated gD gene or gene fragment was subsequently inserted into a plasmid vector to form a recombinant plasmid which serves as a biologically functional replication unit. This recombinant plasmid was constructed so as to facilitate both the replication and expression of the gD gene upon transformation of compatible host cells. Additionally, the plasmid provided for a one-step identification of transformed microorganisms actively expressing the gD gene. Finally, methods are described for isolating the expressed gene product and for use in formulating a vaccine.

4. DESCRIPTION OF THE FIGURES

The present invention may be more fully understood by reference to the following detailed description of the invention, examples of specific embodiments of the invention, and the appended figures in which:

FIG. 1*a* represents the HSV-1 genome and indicates the location of the short unique region (Us) wherein lies the gD gene.

FIG. 1*b* represents a restriction map of the HSV-1 Eco RI-H fragment insert of lambda gtWES::EcoRI-H. Only the restriction sites relevant to the discussion are depicted. Restriction enzymes are abbreviated as follows: Eco RI (RI); Sac I (Sc); Pvu II (Pv); Hind III (H3); Xho I (Xh); Kpn I (Kp); Sal I (Sa); BstE II (Bs); Bgl III (Bg); Bam HI (Ba4 through Ba8).

FIG. 1*c* represents the construction of pRWF6 which comprises an insertion of the Bam HI-8 to Bam HI-7 fragment of lambda gt WES: Eco RI-H inserted into pBR322.

FIG. 1*d* represents the restriction map of the HSV-1 Sac I DNA fragment insert of pSC30-4. The bar (broadened area) represents the location and position of the gD-mRNA coding sequence.

FIG. 2 represents the sequencing strategy and restriction map of the gD gene sequence. The coding region is represented by a bar (broadened area) and the non-coding region by a single line. Restriction endonuclease cleavage sites used for fragment isolation, labeling and secondary digestion are indicated. Horizontal arrows represent the regions of DNA sequenced: those above the restriction map indicate that the non-coding strand sequence was determined; those below the restriction map indicate that the template strand was sequenced.

FIG. 3 represents the nucleotide sequence of the gD gene and the predicted amino acid sequence of the gD protein. Pertinent restriction sites are indicated and the numbered vertical arrows indicate ligation sites of the gD amino-coding terminus to pJS413 thus forming recombinant plasmids pEH51, pEH60, pEH62, pEH66, pEH71, pEH73 and pEH74 which are described more fully in Section 6.6.

FIG. 5 represents the DNA sequence and predicted amino acid sequence of the cro/gD junction in pEH25.

Figure 9:
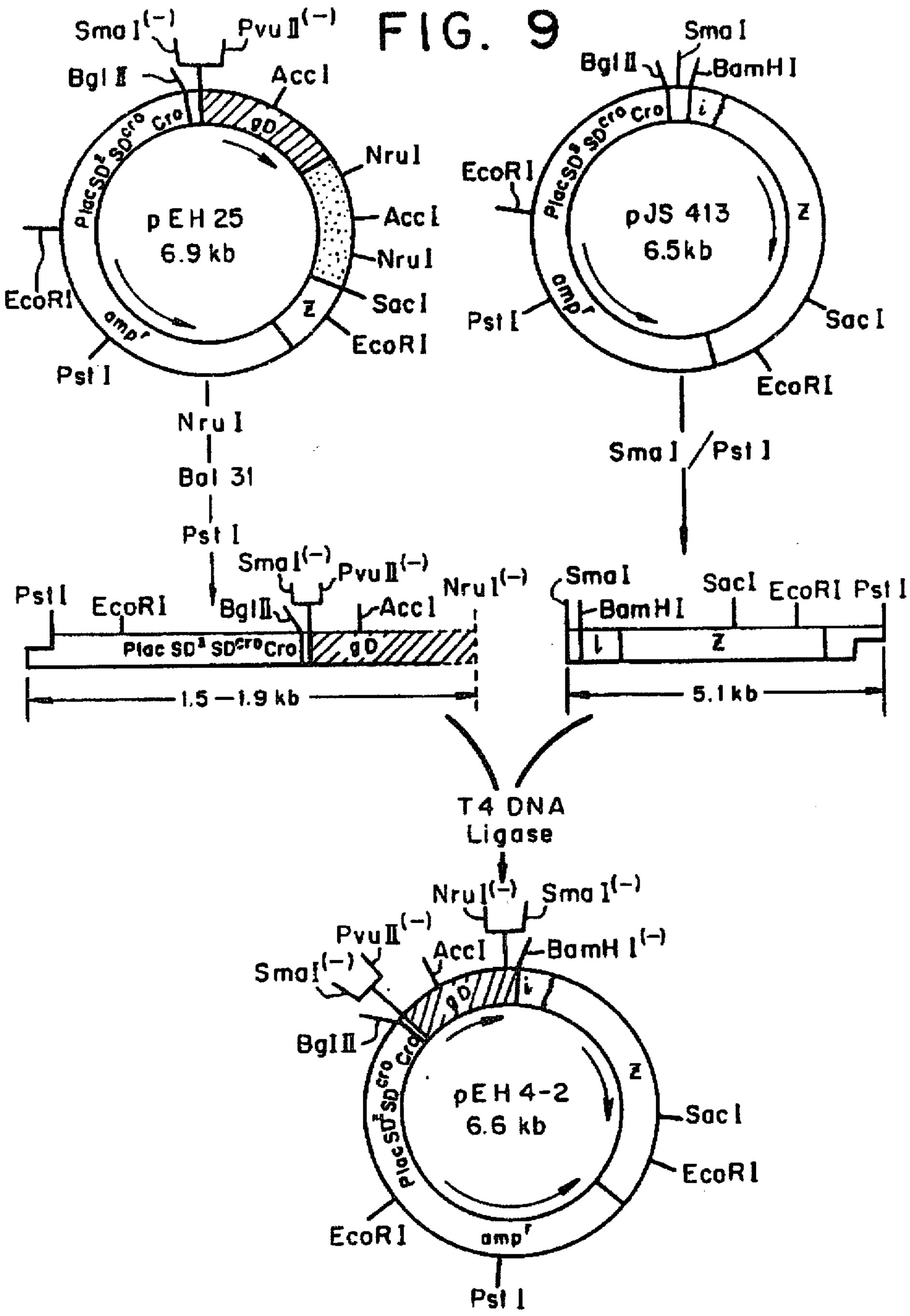

FIG. 9 represents the production of pEH4-2, a gD expression plasmid derived from pEH25, in which 210 nucleotides (70 amino acids) of the 3'-terminus of the gD gene are deleted and replaced with approximately 3,000 additional nucleotides coding for the β-galactosidase protein of *E. coli.* This recombinant plasmid allows for the production of a "sandwich" protein (or fusion protein) with *E. coli*-related peptides (i.e., cro and β-galactosidase) fused to both ends of the gD-specific protein.

Figure 10:
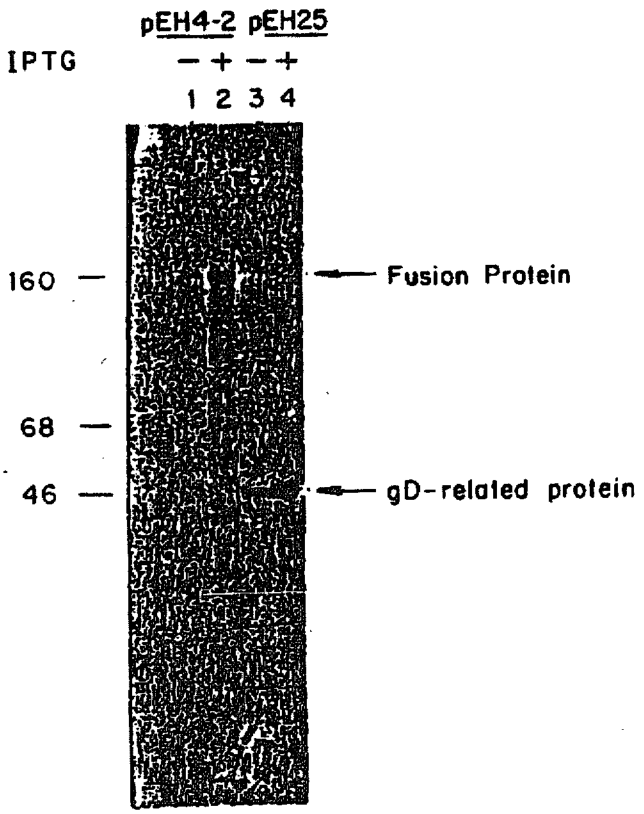

FIG. 10 represents an autoradiograph of pEH4-2 and pEH25-directed polypeptides which immunoreact with rabbit antisera directed against HSV-1.

Figure 11:
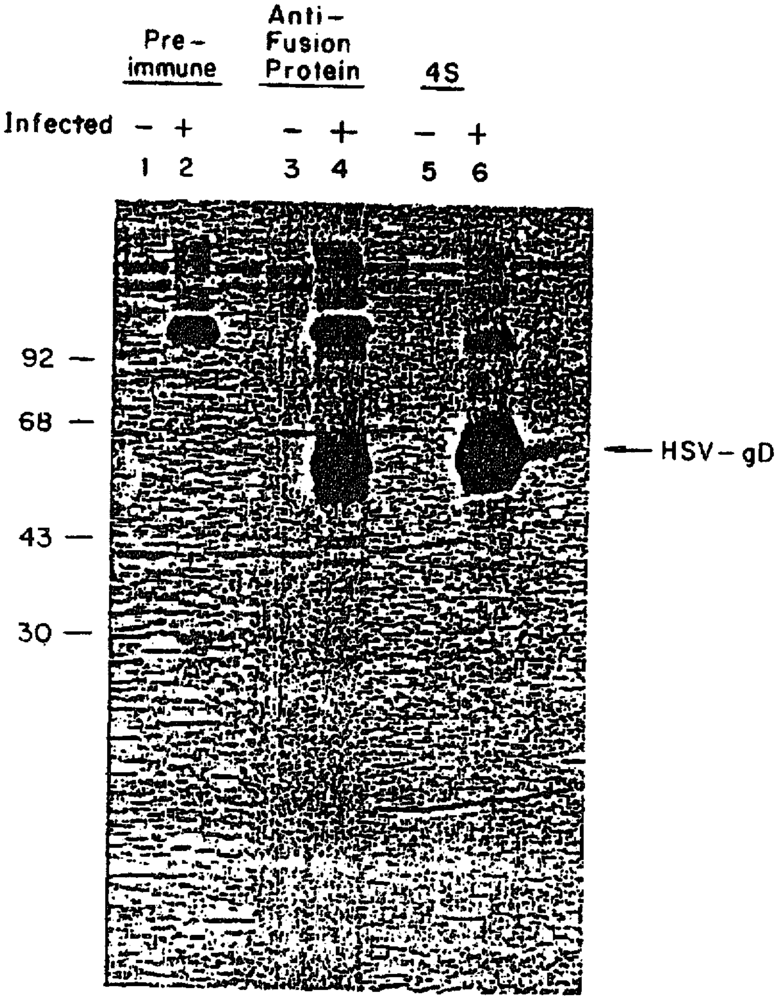

FIG. 11 represents a fluorograph of HSV-1 proteins which were immunoprecipitated by either rabbit antisera directed against pEH4-2 fusion protein or by monoclonal antibody 4S.

Figure 12:
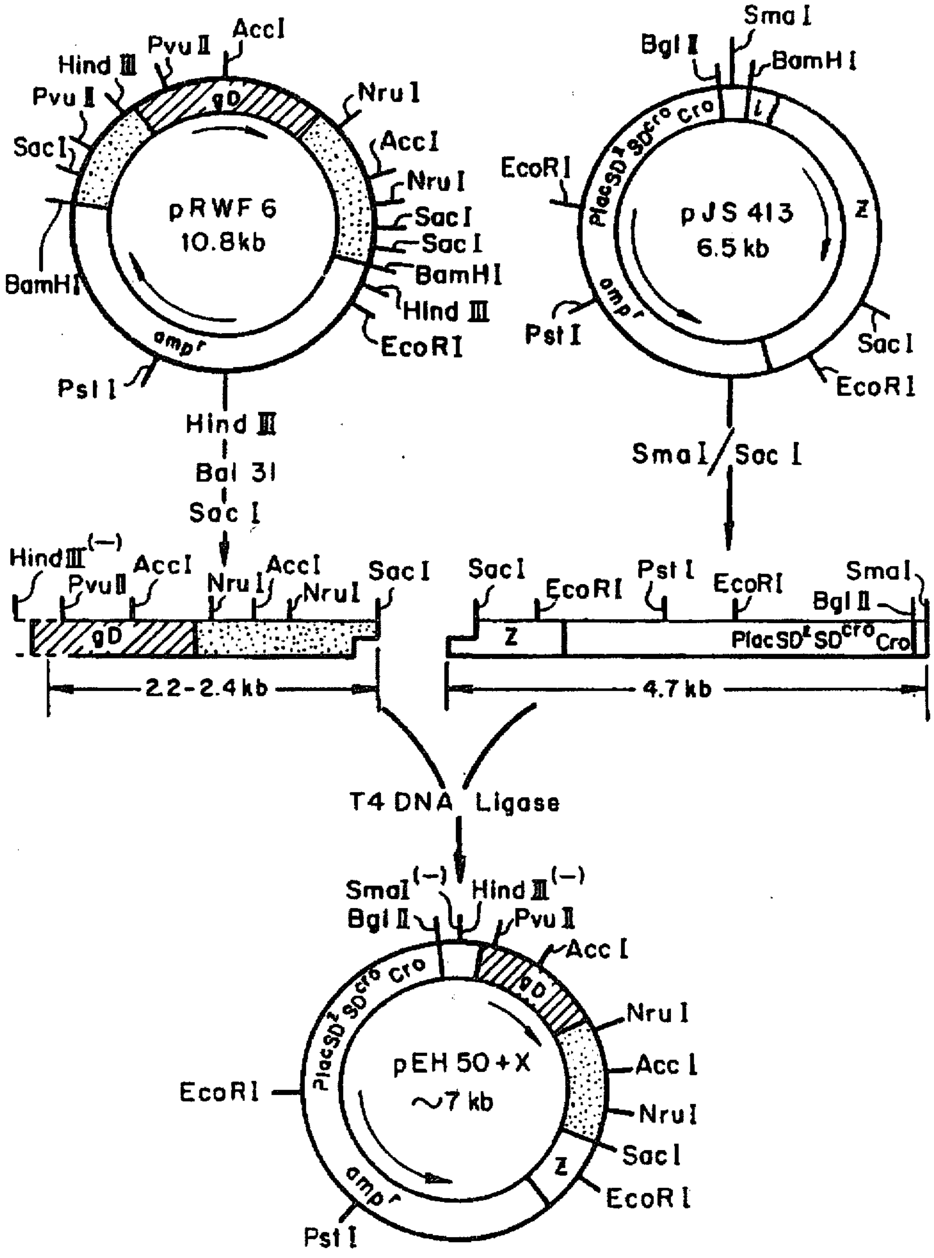

FIG. 12 represents a method for producing a number of gD expression plasmids, pEH50-x, each containing a variable portion of the amino coding terminus of the gD gene.

Figure 13:
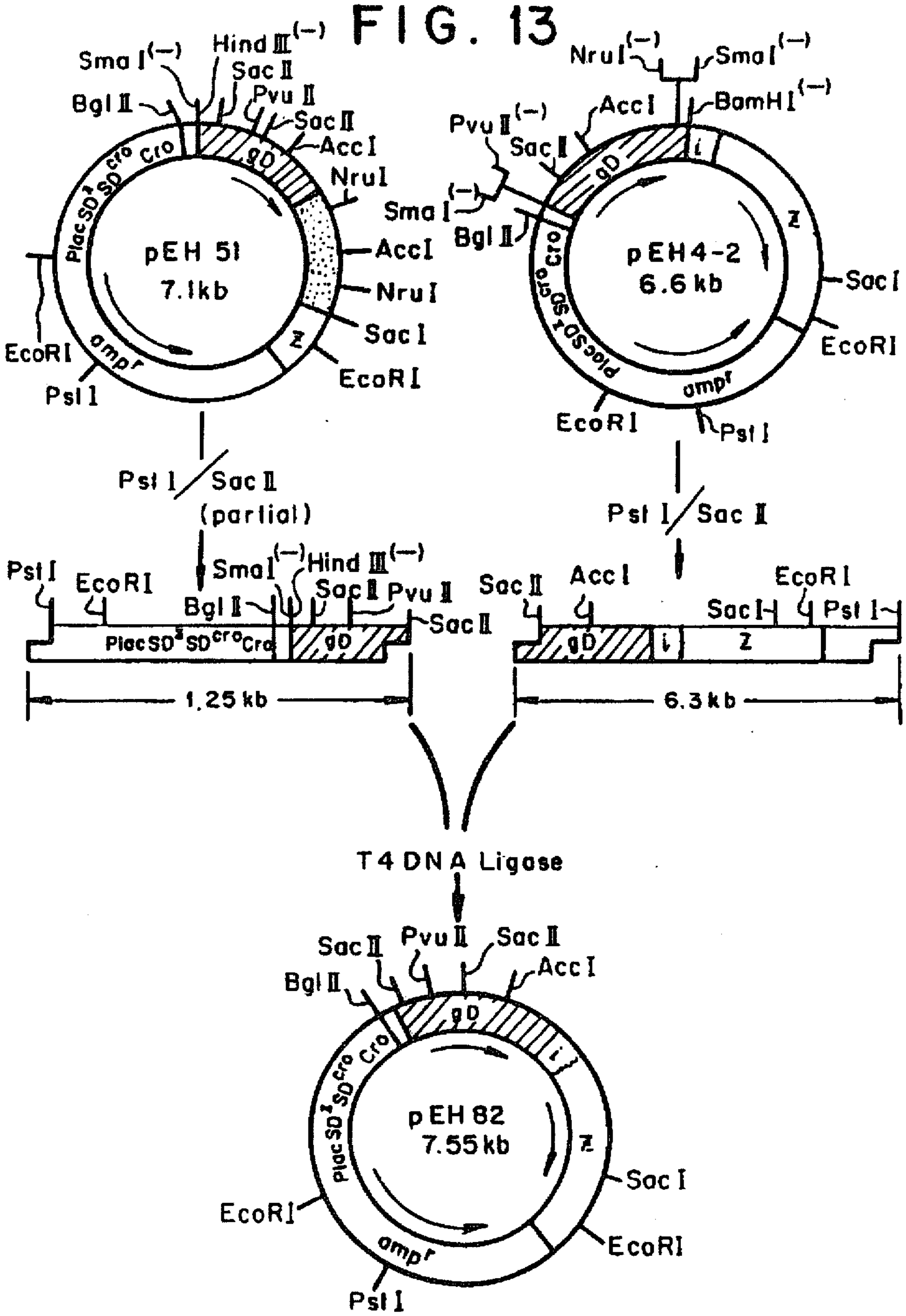

FIG. 13 represents a method for reconstructing the amino-coding terminus of the gD gene in pEH4-2 so that a gD protein fused to β-galactosidase is expressed by host cells transformed with pEH82.

5. DESCRIPTION OF THE INVENTION

This invention relates to the use of recombinant DNA techniques to produce HSV polypeptides which can be used as immunogens in vaccine formulations. More specifically, the production of a gD-related protein is described. Since polyvalent antiserum directed against HSV-1 gD is capable of neutralizing both HSV-1 and HSV-2, the pure gD protein, or any antigenically significant portion thereof, may be used in a subunit vaccine which would efficiently protect the recipient from both HSV-1 and HSV-2 primary infections.

The recombinant plasmids, constructed as described herein, provide for host cell production of a protein which is a gD-related polypeptide and which is stable and resistant to host cell degradation; such plasmids enable the generation of large quantities of a gD-related protein or fusion protein containing immunological and antigenic determinants of gD. However, the DNA compositions described herein are not limited to the production of a gD-related protein and may be used to produce polypeptides related to any of the HSV proteins. It can readily be seen that various immunogens and vaccine formulations can be prepared.

The method of this invention may be divided into the following stages for the purpose of description: (1) identification and isolation of the HSV glycoprotein gene or gene fragment, (2) insertion of the gene or gene fragment into a cloning expression vector to form a recombinant DNA molecule which is used to transform single-cell organisms, (3) identification and growth of the transformed single-cell organisms which are capable of replicating and expressing the gene, (4) identification and purification of the gene product and (5) determination of the immunopotency of the gene product by assessment of its ability to elicit the production of neutralizing antibodies. For purposes of clarity the entire method will be discussed in terms of the gD gene. The same techniques, however, may be applied in an analogous fashion to similarly produce a polypeptide related to any of the HSV glycoproteins.

5.1 IDENTIFICATION AND ISOLATION OF HSV GLYCOPROTEIN GENES

The HSV glycoprotein (gD) gene may be obtained from any HSV type 1 or type 2 strain. Isolation of the gD gene (or a portion thereof), involves first isolating HSV DNA; generating HSV DNA fragments; and identifying the fragments which contain the glycoprotein gene sequences. Before identification, the HSV DNA fragments are usually ligated into cloning vectors that are used to transform host cells; this enables generation of multiple copies of the HSV DNA fragments so that an ample supply is available for analysis and identification procedures.

The HSV DNA can be obtained either (1) by isolating DNA directly from virus purified from eucaryotic cells infected with the virus or (2) from bacteriophage or plasmids which contain a portion of the viral genome containing the gD gene.

In order to generate the HSV DNA fragments, the DNA may be cleaved at specific sites using restriction enzymes; alternatively, one can use DNase in the presence of manganese to fragment the DNA; or the DNA can be physically sheared, as, for example, by sonication. The linear DNA fragments can then be separated according to size by standard techniques, including, but not limited to, agarose and polyacrylamide gel electrophoresis and column chromatography.

Any restriction enzyme or combination of restriction enzymes may be used to generate the HSV DNA fragment containing the gD sequence provided the enzymes do not destroy the immunopotency of the gD gene product. For example, an antigenic site of a protein can consist of from about 7 to about 14 amino acids. Thus, a protein of the size of gD may have many discrete antigenic sites, possibly thousands considering overlapping sequences, secondary structure considerations, and processing events such as acetylation, glycosylation or phosphorylation. Therefore, many partial gD gene sequences could code for an antigenic site. Consequently, many restriction enzyme combinations may be used to generate DNA fragments which, when inserted into an appropriate vector, are capable of directing in a single-cell organism the production of gD specific amino acid sequences comprising different antigenic determinants.

Transformation of host cells with these recombinant DNA molecules incorporating the HSV DNA fragments enable generation of multiple copies of the viral DNA which can then be analyzed to identify the fragment that contains the gD gene sequence. Insertion of HSV DNA restriction fragments into a cloning vector is easily accomplished when the cloning vector has complementary cohesive termini. However, if the complemetary restriction sites used to fragment the HSV DNA are not present in the cloning vector, the ends of the HSV DNA or the cloning vector may be modified. Such modifications include producing blunt ends by digesting back single-stranded DNA termini or by filling in single-stranded termini so that the ends can be blunt end ligated. Alternatively, any site desired may be produced by ligating nucleotide sequences (linkers) onto the DNA termini; these ligated linkers may comprise specific chemically synthesized oligonucleotides encoding restriction site recognition sequences. According to other methods, the cleaved vector and the HSV DNA fragment may be modified by homopolymeric tailing. (For a review see Morrow, 1979, Methods in Enzymology 68: 3.)

Identification of the specific DNA fragment containing the gD gene may be accomplished in a number of ways. Firstly, it is possible to sequence the viral DNA fragments (Maxam and Gilbert, 1980, Methods in Enzymology 65: 499) and then identify the fragment containing the gD gene sequence based upon a comparison of the predicted amino acid sequence to the amino acid sequence of the gD protein. Secondly, the fragment containing the gD gene may be identified by mRNA selection. The HSV DNA fragments are used to isolate complementary mRNA's by hybridization. Immunoprecipitation analysis of the in vitro translation products of the isolated mRNAs identifies the mRNA and, therefore, the complementary HSV DNA fragments that contain gD gene sequences. Finally, gD-specific mRNAs may be selected by adsorption of polysomes isolated from HSV-infected cells to immobilized monoclonal antibodies directed against gD. A radiolabeled gD mRNA or cDNA can be synthesized using the selected mRNA (from the adsorbed polysomes) as a template. The radiolabeled mRNA or cDNA may then be used as a probe to identify the HSV DNA fragments containing gD sequences (Southern, 1975, J. Mol. Biol. 98: 503; Alwine et al., 1979, Methods in Enzymology, 68: 220).

Alternatives to isolating the gD gene include, but are not limited to, chemically synthesizing the gene sequence itself (provided the sequence is known) or making cDNA (complementary DNA) to the mRNA which encodes the gD gene. To accomplish this, mRNA specific for gD is isolated from virus-infected cells. By standard techniques the isolated mRNA is then converted to a cDNA copy and inserted directly into a cloning vector.

Transformation of host cells with recombinant DNA molecules that incorporate the isolated gene, cDNA or synthesized DNA sequence enables generation of multiple copies of the gene. Thus, the gene may be obtained in microgram quantities by growing transformants, isolating the recombinant DNA molecules from the transformants and retrieving the inserted gene from the isolated recombinant DNA. Al ternatively, microgram quantities of the gD gene may be obtained from the source of the gD gene, e.g., herpes simplex virus in infected animal cells, or bacteria or phage containing the viral gene in recombinant plasmids. The viral or plasmid DNA is isolated, fragmented, fractionated and sized by the same methods which may be used to locate the gene.

5.2 INSERTION OF THE HSV GLYCOPROTEIN GENE INTO A CLONING EXPRESSION VECTOR

Once isolated, the gD gene or gene fragment is inserted into an appropriate expression vector, i.e., a vector which contains the necessary elements for transcription and translation of the inserted gene (see Roberts and Lauer, 1979, Methods in Enzymology, 68: 473). To obtain efficient expression of the gD gene (or a portion of the gene), a promoter must be present in the expression vector. RNA polymerase normally binds to the promoter and initiates transcription of a gene or a group of linked genes and regulatory elements (called an operon). Promoters vary in their "strength", i.e., their ability to promote transcription. For the purpose of molecular cloning it is desirable to use strong promoters in order to obtain a high level of transcription and, hence, expression of the gene. Depending upon the host cell system utilized, any one of a number of suitable promoters may be used. For instance, when cloning in an *E. coli* host cell system, any of the promoters isolated from *E. coli*, its bacteriophages or plasmids may be used (e.g., the lac promoter). Additionally, *E. coli* promoters produced by recombinant DNA or other synthetic DNA techniques may be used to provide for transcription of the inserted gene. More specifically, the $P_R$ and $P_L$ promoters of coliphage lambda direct high levels of transcription of adjacent DNA segments. In addition, the recA promoter from *E. coli* provides for high levels of gene transcription of adjacent fragments.

Specific initiation signals are also required for efficient gene transcription and translation in procaryotic and eucaryotic cells. These transcription and translation initiation signals may vary in "strength" as measured by the quantity of gene specific messenger RNA and protein synthesized, respectively. The DNA expression vector, which contains a promoter may also contain any combination of various "strong" transcription and/or translation initiation signals. Thus, any SD-ATG combination that can be utilized by host cell ribosomes may be employed; such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other synthetic technique may be used.

Any of the methods previously described for the insertion of DNA fragments into a vector may be used to ligate a promoter and other control elements into specific sites within the vector.

Accordingly, the gD gene (or any portion thereof) can be ligated into an expression vector at a specific site in relation to the vector promoter and control elements so that the gD gene sequence is in the correct reading frame (i.e., in phase) with respect to the vector ATG sequence. The resultant recombinant DNA molecule is then introduced into appropriate host cells by transformation, transduction or transfection (depending upon the vector/host cell system). Transformants are selected based upon the expression of appropriate gene markers normally present in the vector, such as ampicillin resistance or tetracycline resistance in pBR322, or thymidine kinase activity in eucaryotic host systems. Expression of such marker proteins indicates that the recombinant DNA molecule is intact and is replicating. The expression vectors, which usually contain a marker function, may include, but are not limited to the following vectors or their derivatives: SV40 and adenovirus vectors, yeast vectors, bacteriophage vectors such as lambda gt-WES-lambda B, Charon 28, Charon 4A, lambda gt-lambda BC, lambda GT-1-lambda B, M13 mp7, or plasmid DNA vectors such as pBR322, pAC105, pVA57, pACY177, pkH47, pACYC184, pUB110, pMB9, pBP325, Col El, pSC101, pBR313, pML21, RSF2124, pCRl or RP4.

In addition, host cell strains may be chosen which inhibit the action of the promoter unless specifically induced. In this way greater than 95% of the vector's promoter's effectiveness may be inhibited in uninduced cells. In certain operons the addition of specific inducers is necessary for efficient transcription and translation of the inserted DNA; for example, the lac operon is induced by the addition of lactose or IPTG (i.e., isopropylthio-B-D-galactoside, an analog of lactose). A variety of other operons, such as trp, pro, etc., are under different controls. The trp operon is induced when tryptophan is absent in the growth media; and the $P_L$ promoter of lambda is induced by an increase in temperature. Thus, expression of the genetically engineered gD protein may be controlled. This is important if the protein product of the cloned gene is lethal to host cells. In such cases, the foreign gene may be replicated but not expressed during growth of the transformants. After the cells reach a suitable density in the growth medium, the promoter can be induced for production of the protein.

5.3 PREPARATION OF FUSION PROTEINS

To maximize the level of gene expression in a specific transformant it maybe desirable to ligate the gene in question to a gene encoding another protein, such as a host cell protein. An additional advantage is obtained if the host cell protein inherently contains an assayable function. the epxression of the ligated genes results in a fusion protein product that can be identified on the basis of its large molecular weight and assayable function. For example, production of a gD/β-galactosidase fusion protein offers several advantages for cloning and expression of gD in an *E. coli* host. First, this allows for an approximation of the level of protein production (hence expression) directed by the vector using a colorimetric assay specific for β-galactosidase activity according to the method of Miller (Experiments in Molecular Genetics, Cold Spring Harbor Press, New York, N.Y., 1972). Second, fusion protein production simplifies the identification and isolation of the protein product. The gD protein produced by *E. coli* transformants is smaller than the gD/β-galactosidase fusion protein and as such would co-migrate with several other host proteins analyzed by SDS-polyacrylamide gel electrophoresis. However, the fusion protin produced can be easily detected and identified by SDS-polyacrylamide electrophoresis (SDS-PAGE) due to its unique large molecular weight.

The present invention is not limited to the production of a β-galactosidase fusion protein; any gene of either eucaryotic or procaryotic origin may be ligated in phase with the gD gene (or any HSV protein gene) to provide advantages similar to the β-galactosidase fusion protein product. Examples include, but are not limited to, galactokinase; trp D, E or leader; pilus genes; and eucaryotic genes, such as thymidine kinase, β-globin, SV-40 T-antigen, or Rous Sarcoma Virus transforming gene.

In order to construct a gene which encodes a fusion protein, the two genes must be joined within their coding sequence such that the reading frame is maintained and uninterrupted by termination signals. Also, as previously explained, if the host cell is a strain which inhibits the action of the promoter, the fusion protein will be produced only in response to induction.

5.4 IDENTIFICATION OF THE GENE PRODUCT

Once transformants which contain the correct DNA construction are identifed, an analysis of the immunoreactivity and antigenicity of the recombinant DNA gD gene product is required. Unless the host cell is capable of glycosylating the gD gene product in the same pattern as naturally occurring HSV-gD, the gD gene product will differ from the natural gD glycoprotein. Thus, immunological analysis is especially important for the gD gene product because the ultimate goal is to use the gD-related protein so produced in a vaccine formulation. The analysis of immunoreactivity is most easily carried out using antisera directed against the gD glycoprotein of HSV-infected cells, whereas antigenicity may be evaluated by determining test animal antisera titers which develop in response to immunization with the gD gene product and the ability of the antisera to neutralize HSV infection.

A variety of antisera are available for analyzing immunoreactivity including polyvalent antibody preparations directed against the whole virus or gD in particular. Greater specificity is obtained by using monoclonal antibodies which recognize only one antigenic site on the gD protein molecule. A variety of monoclonal antibodies directed against gD exist, some of which not only specifically immunoprecipitate the gD gene product of HSV-1 and HSV-2 but also neutralize the infectivity of either virus.

Identification of the protein described in this invention is, therefore, based upon two requirements. First, the gD-related protein should be produced only in response to induction of the promoter. Second, the gD-related protein should be immunoreactive using a variety of polyclonal antibodies directed against HSV or monoclonal antibodies directed against gD; the protein should be immunoreactive whether it results from the expression of the entire gene sequence, a portion of the gene sequence or from two or more gene sequences which are ligated to direct the production of a fusion protein. This reactivity may be demonstrated by standard immunological techniques, such as immunoprecipitations, immunodiffusion, radio-immune competition, immunoelectrophoresis or the immunological detection of proteins which were separated by polyacrylamide gel electrophoresis and then transferred to nitro-cellulose.

5.5 PURIFICATION OF THE GENE PRODUCT

Cells containing the gD gene (or any HSV-glycoprotein gene) are grown up in a large volume and the protein produced after induction of the promoter is isolated from such cells or from the medium if the protein is excreted. The protein may be isolated and purified either by standard chromatography including ion exchange, affinity or sizing resins, by centrifugation, or by any other standard technique for the purification of proteins.

A method for protein isolation which is useful for isolating fusion proteins is outlined as follows the cell pellet is quick frozen using dry ice/methanol, weighed, and 3–4 g of cells are resuspended in at least 25 ml of a buffer solution [50 mM Tris-HCl (tris hydroxymethylaminomethane-hydrochloride) (pH 8.0), 2 mM EDTA (ethylenediaminetetraacetic acid) and 200 mM NaCl]. That is, the cells are suspended in a buffer solution at an approximate concentration of from about 100 to 200 grams of cells/liter. Concentrations less than about 160 grams/liter are preferred. To this suspension lysozyme is added to a final concentration of about 130 μg/ml and the resulting mixture is allowed to stand at 4° C. for 20 minutes with occasional shaking. Nonidet P40 (NP-40, Shell trademark, polyoxyethylene (9) p-tert-octylphenol), a non-ionic detergent used to solubilize membranes, is added to a final concentration of about 0.1% and the solution mixed. Then, the suspension is ground for approximately 1 minute using a Polytron (Brinkman Instruments, Westbury, N.Y.) grinder.

The suspension is centrifuged at 10,000 x g for 30 minutes, and the pellet resuspended in a wash buffer of 20 mM Tris-HCl, pH 7.2, 1 mM EDTA, 150 mM NaCl and 2% Triton-X 100, a non-ionic detergent, and ground with the Polytron grinder. This step of centrifugation, washing, and grinding may be repeated to further wash the pellet and remove as much cellular debris as possible.

The suspension is centrifuged, the supernatant removed completely and the pellet resuspended in about one-fifth volume of 6M guanidine hydrochloride (in water). For instance, 3 g of cells washed with 25 ml of buffer should be resuspended at this step in 5 ml of 6M guanidine hydrochloride solution. It may be difficult to resuspend the pellet at this stage and sonication or homogenization may be required in order to obtain a homogenous solution. The solution is allowed to stand at 22° C. for 20 minutes and is then centrifuged at 10,000 x g for 30 minutes to remove debris, saving the supernatant which at this point contains the fusion protein.

The fusion protein is precipitated from the guanidine hydrochloride eluate by the addition of about four volumes of buffer. Almost any buffer may be used at this stage; however, the addition of small amounts of nonionic detergent, such as 0.5% NP40 may be helpful. This suspension is allowed to stand at 4° C. for 30 minutes and is then centrifuged at 3,000 x g for 10 minutes. The supernatant is discarded, the pellet (containing the fusion protein precipitate) is resuspended in Phosphate Buffered Saline (PBS) in the same volume used for the guanidine hydrochloride resuspension. Brief sonication or use of a Polytron may aid in obtaining a homogeneous solution or slurry.

5.6 FORMULATION OF A VACCINE

The purpose of this invention is to produce, by recombinant DNA techniques, an HSV glycoprotein-related polypeptide, such as a gD-related protein, which may be used as an immunogen in a vaccine to protect against HSV-1 and/or HSV-2 infections. If the gD-related protein produced is immunoreactive to specific HSV-1 and/or HSV-2 neutralizing antibodies, it would be expected that the gD-related protein would elicit an immune response capable of neutralizing the relevant virus in vivo. Vaccines made from genetically engineered immunogens should be safer than conventional vaccines made from attenuated virus because there is no risk of infection of the recipient. Alternatively, the genetically engineered gD product may be used to produce antibodies for use in passive immunotherapy.

Although the gD/β-galactosidase fusion protein product itself may be useful in a vaccine formulation, it ay be necessary to first remove the β-galactosidase moiety in order to produce an unfused gD-related protein. Alternatively, reconstruction of the amino-coding terminus of the gD gene may be important for immunogenicity of the protein because the amino terminus may contain additional significant antigenic sites. The amino-coding terminus of the gD gene may be reconstructed by ligating a DNA sequence which encodes the amino terminus of gD into the appropriate site within the gD-coding region of the recombinant DNA molecule. Since the recombinant DNA molecule retains all the necessary expression control elements, a full length (or nearly full length) gD-related protein is produced by cells transformed with the DNA molecule containing the reconstructed gene.

Finally, the genetically engineered gD-related protein is isolated and purified from the host cells using standard protein isolation techniques. The final purified product may then be diluted to an appropriate concentration and formulated with any suitable vaccine adjuvant and packaged for use. Suitable adjuvants include but are not limited to: surface active substances, e.g., hexadecylamine, octadecylamine, lysolecithin, dimethyldioctadecylammonium bromide, N,N-dioctadecyl-N'-N-bis(2- hydroxyethyl-propane diamine), methoxyhexadecylglycerol, and pluronic polyols; polyanions, e.g., pyran, dextran sulfate, poly IC, polyacrylic acid, carbopol; peptides, e.g., muramyl dipeptide, dimethylglycine, tuftsin; oil emulsions; and alum. Finally, the protein product may be incorporated into liposomes for use in a vaccine formulation, or may be conjugated to polysaccharides or other polymers.

The genetically engineered DNA molecules described herein allow great flexibility for vaccine production. For example, a vaccine could be formulated using a gD-related protein produced by transformants containing any portion of the gD gene sequence or a recombinant DNA molecule which contains multiple copies of the gD gene (or portion thereof) in tandem. The gD gene sequence (or portion thereof) may be ligated to genes that encode other immunogens so that the fused protein product could be used in the preparation of multivalent vaccines. Additionally, the gD gene sequence (or portion thereof) could be ligated to other HSV glycoprotein gene sequences (or portions thereof) in any combination. Finally, the gD sequence may be reorganized to increase the immunogenicity of the vaccine. For example, the gene sequence may be altered so that the protein product presents specific epitopes to the immune system (e.g., an antigenic site of gD that is normally unexposed may be presented to the immune system); or the regions of the gD gene sequences that encode immunosuppressive portions of the protein can be deleted.

6. EXAMPLE

According to the method of the present invention the gD gene was located and identified by inserting DNA fragments of the Us portion of the HSV-1 genome (see FIG. 1*a*) into the vector pBR322 to form recombinant plasmids, each of which contained a different fragment of the HSV-1 genome. The plasmid containing the gD gene was identified using three techniques (not necessarily in the order listed): (1) DNA sequencing, (2) gD specific mRNA hybridization studies and (3) in vitro translation of mRNA which hybridizes to the recombinant plasmids.

Once the plasmid containing the gD gene was identified, the gene was characterized by DNA sequencing and by locating the gD gene termini within the recombinant plasmid. A DNA fragment which contained the gD gene lacking the first 156 nucleotides of the coding sequence was isolated from the identified plasmid. This DNA fragment was ligated into a DNA vector, pJS413, to produce pEH25 which was used for cloning and expression of the gene in *E. coli*. The gene product isolated from induced transformants was identified as a gD specific protein by immunoprecipitation with monoclonal antibodies directed against gD and with polyvalent antibodies directed against HSV-1.

Finally, the gD gene fragment was isolated from pEH25 by restriction endonuclease cleavage at specific sites so that the termination sequence (TAG) of the gD coding sequence was deleted. This DNA fragment which containeda portion of the gD gene and the plasmid promoter and control elements (e.g., SD-ATG) was ligated into a vector containing a β-galactosidase coding sequence. The resultant recombinant plasmid, pEH4-2, which contained the gD coding sequence sandwiched between the plasmid's lac promoter with a cro SD-ATG and the β-galactosidase gene, directed the expression of a fusion protein in induced *E. coli* transformants. This fusion protein was then isolated from host cell lysates and formulated for use as an immunogen. Alternatively, the amino-coding terminus of gD gene was reconstructed and the resultant gD protein was formulated for animal injections and pre-clinical trials. A detailed description of each step in the construction is presented in the subsections below.

The gD-related proteins and the gD-fusion proteins produced herein are non-glycosylated and thus differ from the naturally occurring HSV-gD glycoprotein. However, the gD-related protein is immunoreactive with antibodies directed against gD.

6.1 GENERAL PROCEDURES USED FOR PREPARATION OF THE PLASMIDS

The following subsections describe the general procedures and materials used for DNA isolation, enzyme reactions and ligation reactions.

6.1.1 PLASMID DNA ISOLATION

Host cell bacteria *Escherichia coli*, (*E. coli*) were transformed (Gautier and Bonewald, 1980, Molec. Gen. Genet. 178: 375) and large (microgram) quantities of plasmid DNA were isolated from cultures of *E. coli* transformants grown in M-9 broth (Miller, Experiments in Molecular Genetics, Cold Spring Harbor Press, New York, N.Y., 1972). Plasmids were isolated from cells in late logarithmic stage of growth using a modification of the method of Guerry et al. (1973, J. Bacteriol. 116: 1063).

6.1.2 CONDITIONS FOR RESTRICTION ENZYME DIGESTIONS

Restriction enzymes used in the present application were obtained from New England Biolabs, Inc., Beverly, Mass., unless otherwise indicated. An enzyme unit is defined as the amount required to digest 1.0 μg of lambda DNA in 15 minutes at 37° C. in a total reaction mixture of 50 μl.

All restriction enzyme total digestions were accomplished under the following conditions: each 1 μg DNA was incubated with 0.5 units of enzyme at 37° C. for 60 minutes in 20 μl buffer. Partial digestions were accomplished by modifying the conditions used for total digestion as follows: each 1 μg DNA was incubated with 0.1 units of enzyme at 37° C. for 15 minutes. Reactions were terminated by the addition of 0.1% sodium dodecyl sulfate (SD). Thus, the reaction conditions were adjusted to obtain an average of one cleavage per DNA molecule.

6.11.3 RESTRICTION ENZYME BUFFERS

The buffer used for Eco RI, Hind III, Pvu II, Bgl II, BstE II or Nru I digestions consisted of: 6.6 mM Tris-HCl (pH 7.4), 60 mM NaCl, 6.6 mM $MgCl_2$ and 6.6 mM β-mercaptoethanol (β-ME).

The buffer used for Bam HI and Sal I digestions consisted of: 6.6 mM Tris-HCl (pH 7.4), 150 mM NaCl, 6.6 mM $MgCl_2$ and 6.6 mM β-ME.

The buffer used for Sac I, Sac II and Sma I digestions consisted of 6.6 mM Tris-HCl (pH 7.4), 6.6 mM $MgCl_2$ and 6.6 mM β-ME.

6.11.4 MODIFICATION OF DNA

Bal 31 nuclease is a multifunctional enzyme that contains a highly specific single-stranded endodeoxyribonuclease activity and a progressive exonuclease activity that simultaneously degrades both the 3'- and 5'-termini of double-stranded DNA (dsDNA). One unit of nuclease Bal 31 (New England Biolabs, Inc. Beverly, Mass.) is defined as the amount required to release 1.0 μg of acid soluble nucleotides from denatured calf thymus DNA (650 μg/ml) in one minute at 30° C. The reaction buffer used for Bal 31 consisted of: 20 mM Tris-HCl (pH 8.0), 600 mM NaCl, 12 mM $CaCl_2$, 12 mM $MgCl_2$, 1.0 mM EDTA and DNA. Incubations were at 30° C.; Bal 31 digests were accomplished by incubating 30 μg of DNA with 0.5 units Bal 31 for 1, 2, 4, 6, 8 and 10 minutes. Reactions were terminated by the addition of EDTA to 50 mM or heat inactivation of Bal 31 (i.e., 65° C. for 10 minutes).

S1 nuclease degrades RNA or denatured DNA (i.e., single-stranded DNA) into mononucleotides, but will not (under proper conditions) degrade double-stranded DNA or DNA/RNA hybrids. One unit of S1 nuclease (Boehringer Mannheim, Indianapolis, Ind.) is defined as the amount of enzyme required to acid solubilize 1 μg of denatured calf thymus DNA in 30 minutes at 37° C. The reaction buffer used for S1 nuclease consisted of 30 mM sodium acetate (pH 4.6), 250 mM NaCl, 1 mM ZnS04 and 5% glycerol. S1 digestions were accomplished by incubating 2000 units of enzyme with 0.1 μg DNA and 20 μg RNA at 45° C. for 30 minutes.

Exonuclease VII (Exo VII) degrades single-stranded DNA (ssDNA). The mechanism of action of Exo VII appears to be that of a processive exonuclease. One unit of Exo VII (Bethesda Research Laboratories, Rockville, Md.) is defined as the amount of enzyme which produces 1 nmol of nucleotide monomers in 30 minutes at 37° C. using linear, denatured [$^3$H]-SV40 DNA as a substrate. The reaction butter used for Exo VII consisted of 10 mM Tris-HCl (pH 7.9) 100 mM NaCl, 10 mM β-ME and 8 mM EDTA. Exo VII digestions were accomplished using 4 units of Exo VII per 0.1 μg DNA in a 250 reaction volume for 1 hour at 45° C.

6.11.5 GEL PURIFICATION OF DNA FRAGMENTS

After restriction enzyme or nuclease treatment, DNA fragments of varying sizes were separated by gel electrophoresis in either agarose or polyacrylamide slab gels at low voltage (approximately 2 volts/cm for agarose gels and 10 volts/cm for polyacrylamide gels), stained with ethidium bromide and visualized under ultraviolet light (Southern, 1979, Methods in Enzymology 68: 152).

In order to recover particular DNA fragments from gels, the appropriate bands were sliced out of the gel and the DNA was electroeluted into dialysis tubing. The DNA was then isolated on DEAE-cellulose, or ethanol precipitated, and resuspended in the appropriate buffer (Smith, 1980, Methods in Enzymology 65: 371).

6.11.6 DNA LIGATION

All ligations were accomplished using T4 DNA ligase (New England Biolabs, Inc., Beverly, Mass.). One unit of T4 DNA ligase is defined as the amount required to yield 50% ligation of Hind III fragments of bacteriophage lambda DNA in 30 minutes at 16° C. in 20 μl of ligase buffer and a 5'-DNA terminus concentration of 300 μg/ml.

DNA ligations were carried out in ligase buffer consisting of: 20 mM Tris-HCl (pH 7.8), 10 mM $MgCl_2$, 60 mM β-ME, 1.0 mM ATP and a DNA concentration ranging from 15–20 μg/ml. Ligation reactions were incubated 4 to 24 hours at room temperature using approximately 300 units of T4 DNA ligase per 10 reaction volume.

6.12 LOCALIZATION AND ISOLATION OF THE gD GENE

Analysis of the proteins specified by HSV-1 x HSV-2 recombinants indicated that the gD gene mapped between 0.9–0.945 genome map units within the Us region of the DNA (Ruyechan et al., 1979, J. Virol. 29: 667). The Us region was fragmented with restriction enzymes and these fragments were inserted into cloning vectors to create various recombinant plasmids, each containing a defined portion of the Us region. These recombinant plasmids were then analyzed in order to locate the gD gene within the Us region. The map position of gD in HSV-1 has recently been reported by Lee et al., 1982, J. Virol. 43: 41.

6.12.1 RECOMBINANT DNA PLASMIDS CONTAINING DEFINED PORTIONS OF THE Us REGION OF HSV-1

Several recombinant plasmids were constructed using the vector, pBR322, and various fragments of the Us region of HSV-1 (Patton Strain). One of these plasmids, designated pRWF6, was found to contain the entire gD gene. A description of pRWF6 follows.

Figure 1:
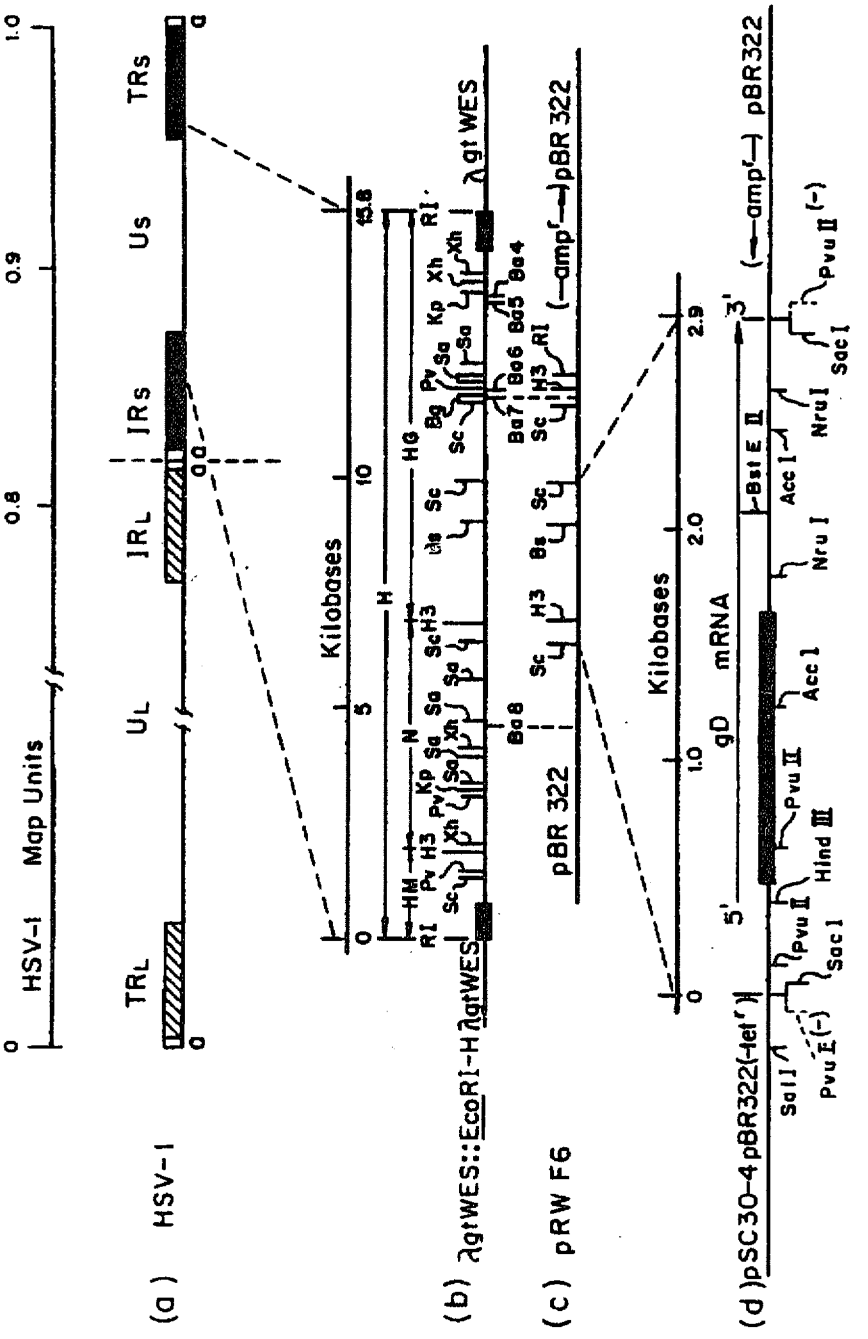

The HSV-1 insert of recombinant plasmid pRWF6 was obtained from the Us region of the lambda gtWES: Eco RI-H clone (Umene and Enquist, 1981, Gene 13: 251). The lambda gtWES: Eco RI-H clone has digested to completion (total digestion) with Eco RI. The Eco RI-H fragment of the lambda gtWES: Eco RI-H clone, approximately 15–16 kb (kilobases), contains the entire Us region of HSV-1 (FIG. 1*b*).

The plasmid, pBR322, and the ECO RI-H fragment (isolated above) of HSV-1 were each totally digested with Bam HI. The resultant 4.4 kb fragment of pBR322 and the 6.4 kb fragment of HSV-1 were annealed and ligated in a 1:1 ratio resulting in pRWF6 (FIG. 1*c*).

6.2.2 LOCALIZATION OF gD SPECIFIC mRNA CODING SEQUENCE

In order to locate and select for the gD-specific coding sequence within pRWF6, the viral DNA insert was subcloned, again into pBR322. Denatured viral DNA restriction fragments of subclone pSC30-4 (described below) were immobilized on nitrocellulose and used to isolate mRNA (via complementary base-pair hybridization) from cytoplasmic RNA extracts of HSV-infected cells. Two mRNA species (3.0 kb and 1.7 kb) hybridized to pSC30-4. Translation of these mRNA species in vitro demonstrated that either the 3.0 kb or the 1.7 kb mRNA encoded the gD protein. Details of the procedure are described below.

The plasmid, pRWF6, was isolated from *E. coli* transformants and digested with the restriction enzyme, Sac I. This generated three fragments: a 6.2 kb fragment containing the entire pBR322 vector plus a portion of the HSV DNA sequence, a 2.9 kb HSV DNA fragment and a 1.7 kb HSV DNA fragment.

In order to subclone the 2.9 kb HSV DNA fragment, pBR322 was cleaved with Pvu II (which linearizes pBR322) and ligated in the presence of Sac I linkers (New England Biolabs, Inc., Beverly, Ma.) using T4 DNA ligase. Thus, the unique Pvu II site of pBR322 was converted to a unique Sac I site [designated Sac I (Pvu II$^{(-)}$)]. After cleavage of the modified pBR322 vector with Sac I enzyme, this vector was ligated with the 2.9 kb HSV Sac I DNA fragment, resulting in pSC30-4 (FIG. 1*d*). This recombinant plasmid was used to transform *E. coli*. Transformants were screened and selected by restriction mapping using a mini-lysate technique (Clewell and Helinski, 1970, Biochem. 9: 4428). The HSV DNA fragment of the subclone pSC30-4 was recovered and used for mRNA hybridization-selection as follows: (Ricciardo et al., 1979, Proc. Natl. Acad. Sci., U.S.A. 76: 4927). The plasmid, pSC30-4, was isolated from L *E. coli* transformants and 200 μg pSC30-4 DNA was digested with Sac I in order to excise the HSV DNA insert. The cleaved plasmid was extracted with chloroform/phenol (1:1) and ethanol precipitated. The pellet was resuspended in 2 ml of 0.3M NaOH and incubated at room temperature for 10 minutes in order to denature the DNA. The suspension was then neutralizd by the addition of 4.4 ml distilled water, 0.2 ml 3M HCl, 0.2 ml 1M Tris-HCl (pH 7.5) and 3 ml 20 x SSC (SSC is 0.15M NaCl, 0.015M sodium citrate). The pH, measured with indicator paper, was between 6 and 8. The denatured, neutralized DNA was vacuum filtered through a 25 mm nitrocellulose filter (Schleicher and Schuell, Keene, N.H.) which was presoaked in distilled water followed by 6 x SSC. After vacuum filtration, the nitrocellulose filters were washed with 6 x SSC and dried at 80° C. for 2 hours. One-half of the nitrocellulose filter was used for the hybridization procedure as outlined below.

The nitrocellulose containing the viral DNA was cut into small pieces and incubated with total cytoplasmic RNA that was isolated from lysates of HSV-infected Vero cells prepared as follows: Vero cells were infected with 10 plaque forming units (pfu)/cell and incubated for 7 hours at 37° C. in Dulbecco's medium with 50 μg/m( cytarabine (β-cytosine arabinoside) added to prevent DNA replication. The cells were lysed with 0.65% NP-40 in 0.15M NaCl, 1.5 mM $MgCl_2$ and 0.01M Tris-HCl (pH 7.9). The nuclei were sedimented by centrifugation at 3000 x g for 2 minutes, and the supernatant was adjusted to a final concentration of 1 mM EDTA (pH 7.9) and 0.5% SDS. The solution was extracted twice with chloroform/phenol (1:1) and once with chloroform. The cytoplasmic RNA was ethanol precipitated (one confluent roller bottle of Vero cells yielded about 1.5 mg RNA) and partially dried. The RNA pellet (about 0.4–0.8 mg RNA) was dissolved in 400 μl hybridization buffer (50% formamide, 0.4M NaCl, 40 mM PIPES, pH 6.4, 1 mM EDTA and 1% SDS) and added to the chopped up nitrocellulose filter. The hybridization was done at 55° C. for 3 hours in a shaking water bath.

The filter pieces were then washed 10 times with SSC containing 0.5% SDS at 60° C., followed by 2 washes with 1 ml 2 mM EDTA in SSC at 60° C. Finally the filter pieces were washed with 2 mM EDTA, pH 8.0, at 60° C. for 5 minutes; the solution was removed and the filter pieces were thoroughly dried with a cotton swab.

The hybridized mRNA was eluted from the nitrocellulose pieces using formamide and heat as follows: 120 μl 95% formamide/10 mM PIPES (pH 6.5) was added to the filters and incubated 5 minutes at 65° C. The eluate was transferred to a microcentrifuge tube and retained on ice. A second 120 μl of the elution buffer was added to the nitrocellulose pieces and incubated again at 65° C. for 5 minutes. This eluate was transferred to a second microcentrifuge tube and retained on ice. A 720 μl aliquot of sterile distilled water was added to the filters which were then agitated. About 360 μl was then transferred to each microcentrifuge tube containing the eluates. To the eluted RNA in the microcentrifuge tubes 20 μl 5M NaCl, 5 μm suitable carrier (e.g., rabbit liver tRNA) and 1 ml absolute ethanol was added. The RNA was precipitated by incubating the mixture for 1 hour at −70° C. or by immersing the tubes in a slurry of dry ice/EtOH for 20 minutes. The precipitated RNA was pelleted (10 minutes at 12,000 x g) in a microcentrifuge and the precipitate of one tube was resuspended in 1 ml buffer (0.5M NaCl, 10 mM Tris-HCl (pH 7.9) and 0.5% SDS) in order to dissolve the RNA. The dissolved RNA was added to the duplicate tube in order to combine aliquots and dissolve all the precipitated RNA. The polyadenylated RNA [poly(A)RNA]was isolated from the dissolved RNA by chromatography using Oligo (dT)-cellulose (Bethesda Research Laboratories, Inc., Rockville, Md.). The poly(A)RNA was eluted from the Oligo(dT) cellulose using 10 mM Tris-HCl (pH 7.9), and 0.1% SDS as the elution buffer; the poly(A)RNA was then ethanol precipitated as previously described.

Two species of mRNA which hybridized to the pSC30-4 DNA were isolated, a 3.0 kb and 1.7 kb mRNA. These two species were translated in vitro using a rabbit reticulocyte cell-free system containing 35S-methionine (Pelham and Jackson, 1976, Eur. J. Biochem. 67: 247).

The in vitro translation extracts were immunoprecipitated with monoclonal antibody 4S which is directed against gD (provided by M. Zweig, National Institute of Health) and prepared for SDS-PAGE as previously described. Electrophoretic analysis of the immunoprecipitated protein products of the cell-free translation system demonstrated that these selected mRNAs specified a 50,000 dalton gD-specific protein (data not shown). According to the size of gD protein, the minimum mRNA coding sequence would be approximately 1.7 kb; thus, taking mRNA leader sequences and poly (A) tails into account, the larger (3.0 kb) mRNA was suspected to encode the gD polypeptide.

6.12.3 CHARACTERIZATION OF THE gD mRNA

Mapping the position of the 3.0 kb mRNA sequence within pSC30-4 and characterizing the mRNA was accomplished by S1 mapping, i.e., using single-strand specific nuclease S1 and Exonuclease VII to map the regions of DNA probes that hybridized to complementary mRNA sequences (Berk and Sharp, 1978, Proc. Natl. Acad. Sci., U.S.A. 75: 1274), and by sequencing the DNA of the gD gene coding region (Maxam and Gilbert, 1980, Methods in Enzymology, 65: 499).

The S1 mapping technique demonstrated that both the 3.0 kb and the 1.7 kb mRNA species were unspliced (i.e., did not contain intervening sequences or introns) and that they had different 5′-termini, but common 3′-termini. A 1608 nucleotide DNA sequence including the coding region at the 5′-terminus of the 3.0 kb mRNA was determined and the reading frame of translation was deduced by locating the initiation codon (ATG) closest to the 5′-terminus.

The principle of the S1 mapping technique is to allow duplex formation between RNA and a radiolabeled single-stranded DNA (ssDNA) probe (e.g., obtained from pSC30-4). If the RNA is a mature spliced mRNA, then the introns will form a ssDNA loop. The enzyme nuclease S1 digests all ssDNA regions of the radiolabeled DNA that are not protected by duplex formation with RNA, whereas Exonuclease VII digests ssDNA only at the termini and, therefore, will not digest the ssDNA loops. Comparison of the size of DNA not susceptible to these nucleases (by virtue of hybridization to RNA) enables the detection of spliced mRNA transcripts.

In the present invention the radiolabeled DNA used to locate the 5′-terminus of the 3.0 kb mRNA was a 3.8 kb Bam HI-8/BstE II fragment of pRWF6 which was labeled with $^{32}P$ (using the enzyme, polynucleotide kinase, according to the method of Maxam and Gilbert, supra) at its BstE II 5′-terminus before cleavage with Bam HI. The radiolabeled DNA used to locate the 3′-terminus of the 3.0 kb mRNA was a 4.7 kb Hind III/Sal I fragment of pSC30-4 which was labeled with $^{32}P$ using the Klenow fragment of DNA polymerase, according to the method of Maxam and Gilbert, supra) at its Hind III 3′-terminus before cleavage with Sal I. Cytoplasmic mRNA was isolated from HSV-infected Vero cells grown for 7 hours in the presence of cytarabine as previously described. The S1 mapping technique used was a modification of the Berk and Sharp procedure (Watson et al., 1981, J. Virol. 37: 431). The 5'-terminus of gD mRNA mapped near the Hind III site of pSC30-4, while the 3'-terminus mapped approximately 2.8 kb downstream (FIG. ld).

Figure 2:
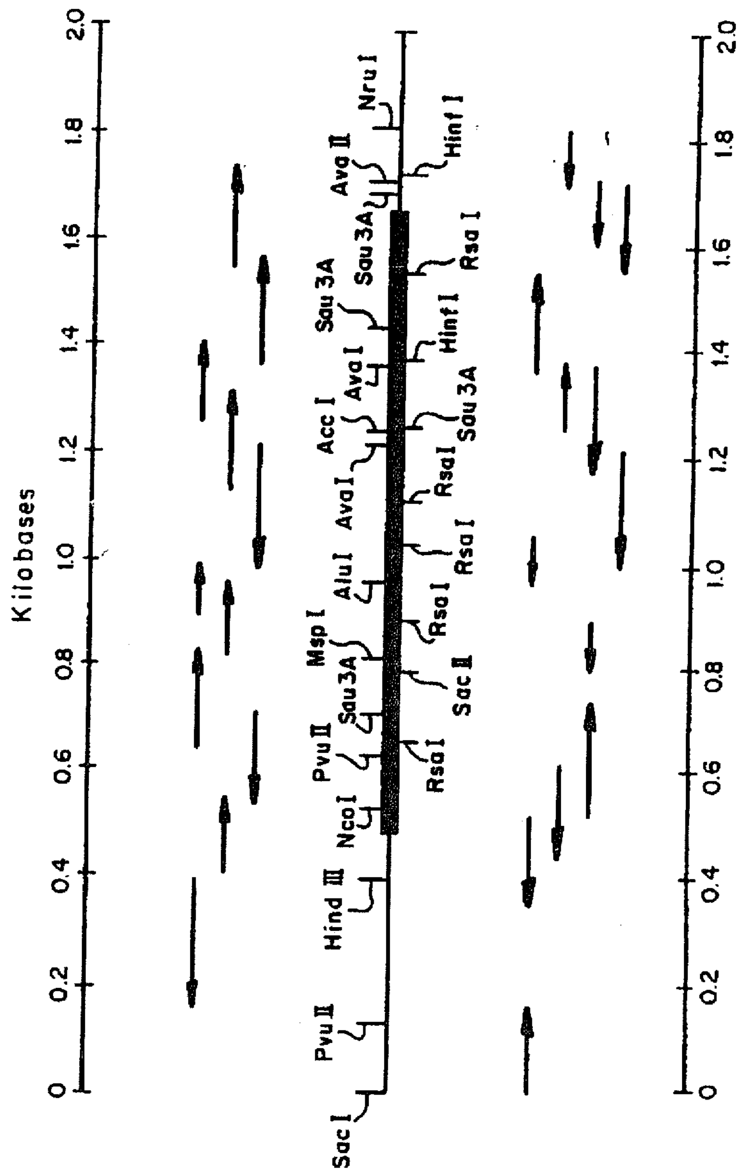

Finally, the HSV DNA of pSC30-4 was sequenced using the Maxam and Gilbert method. FIG. 2 demonsrates the sequencing strategy for the HSV-1 gD gene coding region. Both the coding and non-coding strands were sequenced. FIG. 3 represents the DNA sequence obtained for the HSV-1 gD gene. It was apparent that the DNA sequence contained an open reading frame of 394 codons extending from an ATG at position 241. This site was suspected to be the initiator of the gD gene and was shown to be so by the cloning of this putative gD gene sequence into expression vector pJS413 (see Section 6.3).

6.13 CLONING AND EXPRESSION OF THE gD GENE

A portion of the putative gD gene (hereinafter referred to as the gD gene), lacking the initiation sequence, ATG, and the first 156 nucleotides of the amino-coding terminus (5'-end of the gene) was ligated into a DNA cloning expression vector, pJS413, to form pEH25. The partial gD gene was inserted so that the protein coding sequence was in the correct reading frame with respect to the initiation ATG of the vector. As a result, subsequent translation of the transcribed mRNA begins at the initiation sequence (ATG) of the vector through the gD gene (lacking its own initiation ATG and the first 156 nucleotides of the gD gene) to the natural termination signal of gD.

The pEH25 plasmids containing the gD gene were used to transform an *E. coli* host strain in which the transcription of DNA from the lac operon is inhibited unless the promoter is specifically induced. Primary transformants were assayed for drug resistance (the ampicillin resistance gene is carried on the vector) and resistant clones were analyzed further. The structure of the resultant recombinant plasmid, pEH25, was verified by restriction analysis and DNA sequencing. Induction of pEH25 transformants resulted in the production of a 46,000 dalton polypeptide that was immunoprecipitable with either antisera directed against HSV or monoclonal antibodies directed against gD. These procedures are described in more detail in the following subsections.

6.13.1 THE EXPRESSION VECTOR pJS413

The expression vector, pJS413 (FIG. 4), is a pBR322 derivative which contains the $amp^r$ ($\beta$-lactamase) gene, a lac promoter (P lac), lac and cro ribosome binding sites ($SD^{lacZ}$ and $SD^{cro}$ are represented in all figures as SDz and SDcro, respectively), a chain initiation ATG with 69 nucleotides of cro (cro), and a modified $\beta$-galactosidase gene (the i-z gene, hereinafter referred to as the z-gene). Insertion of a gene in the correct reading frame between the cro initiation ATG of pJS413 and the z-gene (i.e., within the Sma I site of pJS413) allows for expression of a fusion protein in transformed cells. In the present example, however, the z-gene was deleted and the partial gD gene was ligated in phase with the pJS413 cro initiation ATG and cro nucleotides.

In order to prepare pJS413 for insertion of the gD gene (see FIG. 4), pJS413 was digested with Sma I (resulting in a blunt end) and Sac I (resulting in a Sac I 3'-cohesive end). The 4.7 kb fragment, containing the promoter, SD sequences, initiation ATG and partial cro sequence, was isolated by gel electrophoresis. The 1.8 kb fragment containing the 5'-terminus of the z-gene was deleted.

6.13.2 INSERTION OF THE gD GENE INTO pJS413

Figure 4:
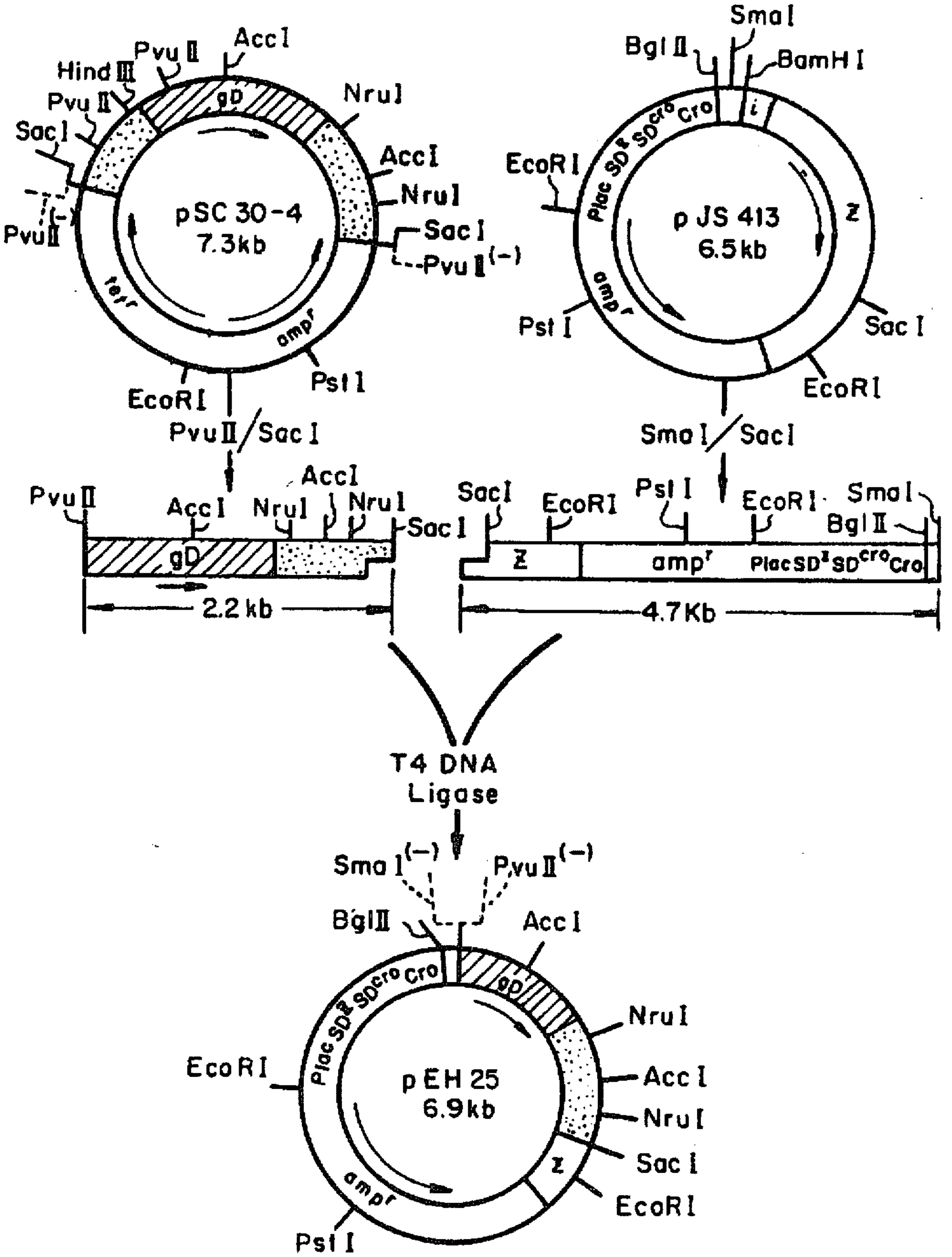
FIG. 4 (not drawn to scale) represents the construction of pEH25, a recombinant plasmid derived from a portion of the HSV-1 gD gene, and pJS413, an expression vector for *E. coli.* The recombinant plasmid, pEH25, directs the production of a gD-related protein encoded by approximately 80% of the gD gene sequence ligated to a "leader" sequence (cro) derived from the expression vector.

After mapping the gD gene within pSC30-4 (Section 6.2.3), a 2.2 kb DNA fragment containing the last 1026 bp (base pairs) of the carboxy-coding terminus of the gD gene was selectively isolated from pSC30-4 by digestion with Pvu II (resulting in a blunt end) and Sac I (resulting in a Sac I 3'-cohesive end) (FIG. 4).

The 2.2 kb Pvu II/Sac I pSC30-4 fragment and the 4.7 kb Sma I/Sac I pJS413 fragment were ligated in a 1:1 ratio using T4 DNA ligase (FIG. 4). The resultant recombinant plasmids were used to transform *E. coli* strain NF1829. The *E. coli* strain NF1829 is a K-12 MC1000 derivative carrying an F'-lac episome with the lac $i^q$ mutation for lac repressor overproduction. The lac z-gene encoding $\beta$-galactosidase present on the F'-lac episome is inactivated by a Tn 5 (transposon) insertion. Thus, in strain NF1829, the lac promoter must be induced in order to obtain expression of a gene inserted into the pJS413 plasmid.

6.3.3 IDENTIFICATION OF TRANSFORMANTS THAT EXPRESS THE gD GENE

The plasmids isolated from ampicillin resistant *E. coli* transformants were analyzed by restriction enzyme mapping and by DNA sequencing of the junction between the pJS413 vector, and the gD gene insert. The plasmid pEH25 (FIG. 4) had the correct nucleotide sequence across the cro-gD junction, as depicted in FIG. 5, and was examined for its ability to direct the expression of a gD-related polypeptide. Since the lac promoter was transcriptionally inactive in NF1829 (due to the overproduction of the lac repressor) the gD protein could only be detected upon induction of the promoter with either 1 mM IPTG or 1-10 mM lactose.

The clone transformed with pEH25 was examined for IPTG-specific induction of the gD-related protein and was found to produce a 46,000 dalton protein consisting of 23 amino acids of cro protein (coded for in pJS413) and 342 amino acids of the gD protein (i.e., the first 52 amino acids of gD are missing). This protein could be immunoprecipitated with total rabbit antisera directed against HSV-1 (DAKO Chemicals, Inc., Hicksville, N.Y.) and with monoclonal antibodies (1S, 4S, 55S and 57S) specifically directed against gD of HSV-1 (Showalter et al., 1981, Infection and Immunity, 34: 684).

Monoclonal antibodies 1S, 4S, 55S and 57S recognize a number of distinct sites on the gD molecule (Eisenberg et al., 1982, J. Virol. 41: 478). Notably, monoclonal 4S is capable of neutralizing HSV-1 and HSV-2 infectivity and immunoprecipitating the gD protein produced by both viruses. The protein produced by pEH25 was immunoprecipitated by the 4S antibody, demonstrating that the pEH25 gD related protein expressed antigenic determinants shared by both HSV-1 and HSV-2 gD proteins. In addition, the pEH25 gD-related protein was immunoprecipitated by the 1S monoclonal antibody that neutralizes only HSV-1. The pEH25 gD-related protein was also precipitated by the 55S and 57S monoclonal antibodies which do not neutralize either HSV-1 or HSV-2 infectivity. Each of the immunoprecipitates was analyzed by SDS-PAGE; details of the entire procedure are explained below.

All pEH25 transformants were grown by removing an aliquot of an overnight culture (stationary phase) in L broth at 37° C., diluting 20-fold in M-9 broth and growing at 37° C. with shaking for 90 minutes (Miller, Experiments in Molecular Genetics, Cold Spring Harbor Press, New York, N.Y., 1972). In assays of these cultures for expression of gD protein, 1 mM IPTG and 25 $\mu$Ci/ml $^{35}$S-methionine were added to the culture (controls were labeled with $^{35}$S-methionine, but were not induced). After 60 minutes at 37° C. the cultures were pelleted by centrifugation. In order to lyse the cells and release the cell contents, each pellet of cells was resuspended in an equal volume of lysis buffer, IP-3 (20 mM Tris-HCl (pH 8.1), 100 mM NaCl, 1 mM EDTA, 1% NP-40, 1% deoxycholate and 0.1% SDS), quick frozen in liquid nitrogen and sonicated. The cell lysate was centrifuged at 5,000 x g for 5 minutes at 4° C., and the supernatant was divided into aliquots. Control sera (non-immune or pre-immune sera) or test antisera (polyvalent antisera directed against HSV-1 or monoclonal antisera directed against gD) was added to each aliquot which was then incubated at 4° C. for 60 minutes. (The amount of antisera added is determined by calibrating the antisera titer by testing serial dilutions of antisera using a known amount of antigen.)

The immune complexes were collected by adding washed Pansorbin (*Staphylococcus aureus* protein A, Calbiochem-Behring Corp., LaJolla, Calif.) and centrifuging (all centrifugations in this procedure were run at 5,000 x g for 5 minutes at 4° C. unless otherwise indicated). The pelleted immunoprecipitate was resuspended and washed with IP-2 (identical to IP-3 but with 20 mg/m( bovine serum albumin, BSA, added to eliminate non-specific adsorption), washed twice with IP-3, and resuspended in IP-1 (20 mM Tris-HCl (pH 8.1), 100 mM NaCl, 1 mM EDTA and 1% NP-40). The suspension was transferred to a new tube in which it was centrifuged and the pellet was resuspended in SDS-polyacrylamide gel sample buffer (Laemmli, 1970, Nature 227: 680). After heating at 95° C. for three minutes, the sample was centrifuged for 2 minutes at 12,000 x g in a microcentrifuge to remove insoluble components. The supernatant was removed and loaded onto an SDS polyacrylamide gel (10%). After electrophoresis the proteins were stained with Coomassie blue dye, treated with sodium salicylate and dried for fluorography (Chamberlain, 1979, Anal. Biochem. 98: 132).

Figure 6:
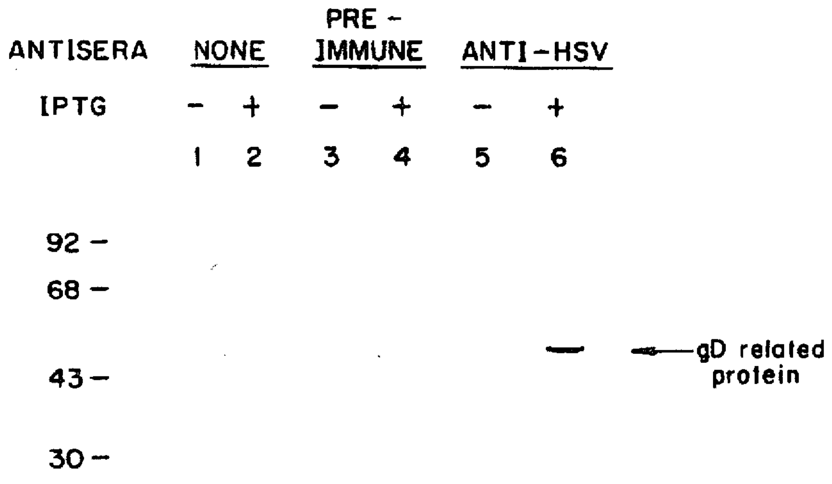
FIG. 6 represents a fluorograph of pEH25-directed proteins which were immunoprecipitated with rabbit antisera directed against HSV-1 and separated by, SDS-PAGE (sodium dodecylsulfate-polyacrylamide gel electrophoresis).

FIG. 6 is a fluorograph which shows the results of these experiments. Cell lysates of $^{35}$S-methionine-labeled *E. coli* (NF1829) transformed with pEH25 were incubated with rabbit antisera. The radiolabeled immunoprecipitated proteins were resolved by SDS-PAGE and fluorographed. Lanes 1, 3 and 5 were derived from uninduced transformants, whereas lanes 2, 4 and 6 were derived from transformants induced with IPTG. The lysates represented by lanes 1 and 2 were not incubated with antisera. The lysates represented by lanes 3 and 4 were incubated with rabbit pre-immune sera. The lysates represented by lanes 5 and 6 were incubated with rabbit antisera directed against HSV-1. Lane 6 clearly demonstrates the immunoreactive pEH25-directed 46,000 dalton gD-related protein produced upon induction.

Figure 7:
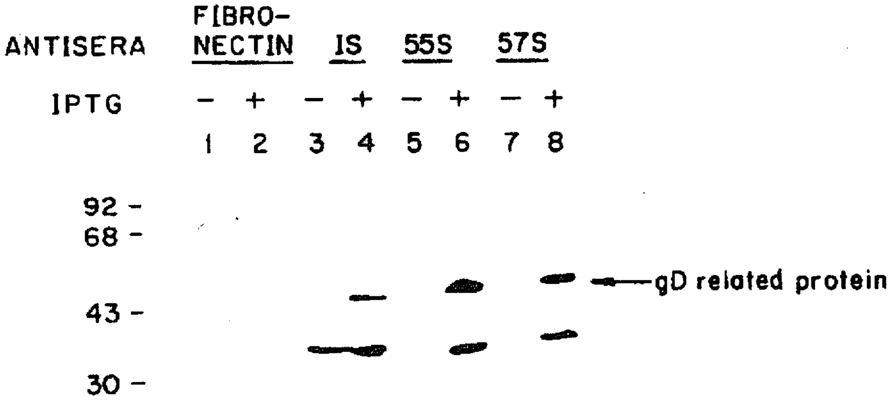
FIG. 7 represents a fluorograph of pEH25-directed proteins which were immunoprecipitated with monoclonal antibodies directed against gD and separated by SDS-PAGE.

FIG. 7 is a fluorograph which demonstrates the results of experiments using monoclonal antibodies 1S, 55S and 57S. Cell lysates of $^{35}$S-methionine-labeled *E. coli* (NF1829) transformed with pEH25 were incubated with various monoclonal antibodies. The radiolabeled immunoprecipitated proteins were resolved by SDS-PAGE and fluorographed. Lanes 1, 3, 5 and 7 were derived from uninduced transformants whereas lanes 2, 4, 6 and 8 were derived from transformants induced with IPTG. The lysates represented by lanes 1 and 2 were incubated with a monoclonal antibody directed against fibronectin. The lysates represented by lanes 3 and 4 were incubated with monoclonal antibody 1S. The lysates represented by lanes 5 and 6 were incubated with monoclonal antibody 55S. The lysates represented by lanes 7 and 8 were incubated with monoclonal antibody 57S. Lanes 4, 6 and 8 reveal that monoclonal antibodies 1S, 55S and 57S (respectively) immunoprecipitate the induced 46,000 dalton gD-related protein.

Figure 8:
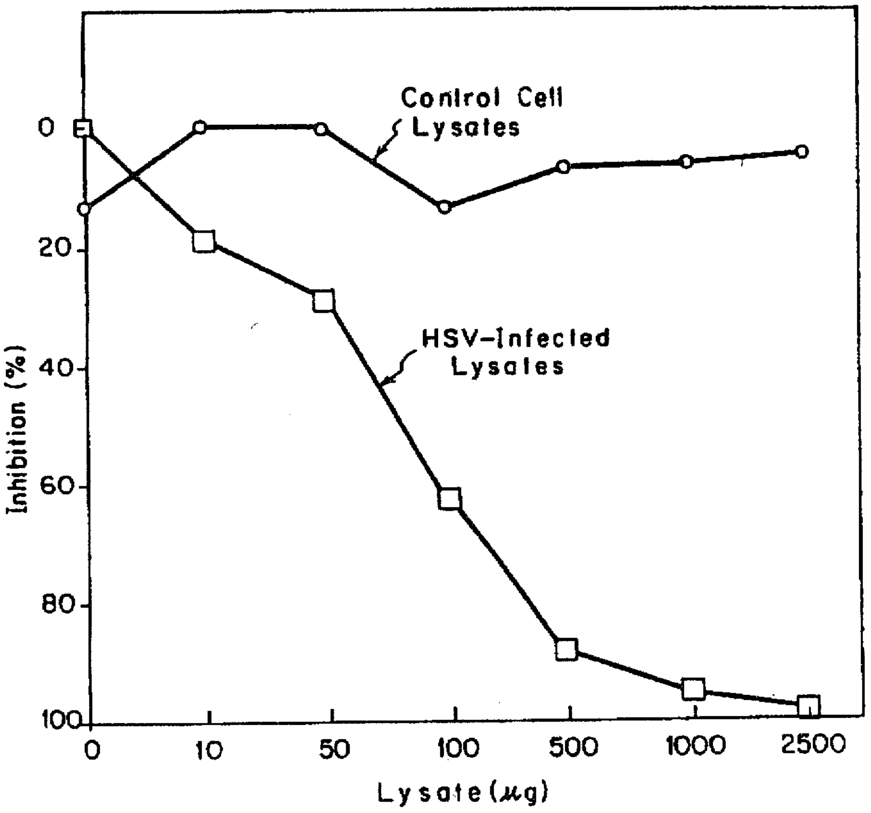
FIG. 8 represents the inhibition of immunoprecipitation of the pEH25 gD product by the addition of competing antigens present in lysates of HSV-infected Hela cells. The open circles represent lysates of uninfected Hela cells (controls); the open boxes represent lysates of the Hela cells infected with HSV-1.

Finally, competition experiments were performed to determine the effect of lysates of HSV-infected Hela cells upon the immunoprecipitation of the induced gD-related protein expressed in *E. coli* NF1829 transformed with pEH25 (see FIG. 8). A serial dilution was made of lysates of control (uninfected) and HSV-1 infected Hela cells (infections were accomplished as previously described for Vero cells). A 5 $\mu$l aliquot of a 100-fold dilution of monoclonal 55S ascites fluid (a gD-specific monoclonal antibody) has added to each aliquot of the dilution series of Hela cell lysates. After incubation at 4° C. for 30 minutes, equal amounts of $^{35}$S-methionine labeled proteins from lysates of induced pEH25 transformants were added to the Hela cell lysates and incubated for an additional 60 minutes at 4° C. The immune complexes were collected by immunoprecipitation and analyzed by SDS-PAGE and fluorography as previously described. The protein band which was specifically immunoprecipitated was sliced out of the gel, and the radioactivity was measured by scintillation counting. FIG. 8 represents the results of these experiments: the radioactivity of each sample, which represents the immunoprecipitated labeled protein product of pEH25, was plotted as a percentage of the control. The open circles represent the serially diluted control (uninfected) Hela cell lysate. The boxes represent the serially diluted HSV-1-infected Hela cell lysate. This clearly demonstrates that HSV-1 proteins successfully compete with radiolabeled pEH25-directed protein for the formation of immune complexes with 55S monoclonal antibody.

6.4 PREPARATION OF pEH4-2 WHICH DIRECTS THE PRODUCTION OF A cro/gD/$\beta$-GALACTOSIDASE FUSION PROTEIN The gD gene was isolated from pEH25 so that its termination signal was deleted. To this end, the DNA fragment containing the gD gene sequence was cleaved at a restriction site beyond the gD termination sequence, TAG; the TAG was then removed by progressive digestion of the termini with Bal 31, a DNA nuclease. This gD gene fragment was then ligated into pJS413 in order to encode a fusion protein: cro/gD/$\beta$-galactosidase. The procedure is described below and depicted in FIG. 9.

The plasmid pEH25 was digested to completion with Nru I and digested progressively with Bal 31 nuclease. The resulting variable length DNA was then cleaved with the restriction enzyme Pst I yielding a spectrum of fragments, many of which lacked the gD termination codon but retained most of the gD gene sequence. The appropriate DNA fragments (1.5–1.9 kb) were isolated by gel electrophoresis and eluted as described previously. The vector pJS413 was digested to completion with Pst I and Sma I and the appropriate 5.1 kb DNA fragment was isolated (FIG. 9). The pEH25 fragment and the pJS413 fragment were ligated at a 1:1 ratio and used to transform *E. coli* NF1829. The ampicillin resistant colonies were examined for fusion protein production by assaying for β-galactosidase activity on indicator agar plates (Miller, Experiments in Molecular Genetics, Cold Spring Harbor Press, New York, N.Y., 1972). The positive colonies were tested for the presence of the cro/gD/β-galactosidase fusion protein by SDS-PAGE analysis of total lysates of transformants induced with IPTG. One high level producer of a 160,000 dalton fusion protein was isolated from those clones expressing the cro/gD/β-galactosidase fusion proteins; the plasmid contained in this clone was designated pEH4-2 (FIG. 9).

6.4.1 ANALYSIS OF THE pEH4-2 FUSION PROTEIN

The fusion protein produced by the *E. coli* clone transformed with pEH4-2 was shown to be inducible by IPTG and to specifically interact with rabbit antisera directed against HSV-1 (data shown in FIG. 10). IPTG-induced proteins of pEH4-2 and pEH25 were separated by SDS-PAGE and transferred to nitrocellulose (i.e., a protein "blot" was done). The nitrocellulose was then treated with rabbit antisera directed against HSV-1 followed by $^{125}$I-labeled goat antisera directed against rabbit immunoglobulin as a probe (Towbin et al., 1979, Proc. Natl. Acad. Sci., U.S.A. 76: 4350).

FIG. 10 is an autoradiogram of the protein blot. Lanes 1 and 3 represent lysates which were derived from uninduced pEH4-2 and pEH25 transformants (respectively). Lanes 2 and 4 represent lysates which were derived from induced pEH4-2 and pEH25 transformants (respectively). Lane 2 clearly demonstrates that the 160,000 dalton pEH4-2-specified fusion protein immunoreacts with rabbit antisera directed against HSV-1. Lane 4 demonstrates that the 46,000 dalton pEH25-specified gD-related protein immunoreacts with rabbit antisera directed against HSV-1.

Antisera directed against the pEH4-2 fusion protein was also shown to be immunoreactive with HSV-1 gD, thus demonstrating that the pEH4-2 fusion protein contains gD-specific antigenic determinants. This was demonstrated by SDS-PAGE analysis of HSV proteins immunoprecipitated with antisera directed against pEH4-2 fusion protein; see FIG. 11 and the discussion which follows.

The rabbit antisera directed against the pEH4-2 fusion protein was produced as follows: the *E. coli* clones transformed with pEH4-2 were grown to mid-log phase and induced with 1 mM IPTG. Four hours after induction the bacteria were pelleted by centrifugation, lysed with SDS-PAGE sample buffer and loaded on preparative SDS-polyacrylamide gels. After electrophoresis, the proteins were visualized by staining the outer lanes with coomassie blue dye; then the 160,000 dalton fusion protein band was sliced from the gel. The gel slice was immersed in liquid nitrogen, ground to a powder and then suspended in an equal volume of Freund's complete adjuvant. After thorough mixing, the solution was injected subcutaneously into two New Zealand rabbits (018 and 019). Each rabbit was injected with 25 to 50 μg protein. After 28 days the rabbits were boosted with the fusion protein suspended in incomplete Freund's adjuvant. The animals were boosted two more times at 10 day intervals. The serum collected 48 days after the initial injection was used for immunoprecipitation analysis.

Lysates of $^{35}$S-methionine-labeled HSV-1-infected GBK (Georgia Bovine Kidney) cells were incubated with rabbit antisera directed against the pEH4-2 fusion protein or with monoclonal antibody 4S. The radiolabeled immunoprecipitated proteins were resolved by SDS-PAGE and fluorographed (FIG. 11). Lanes 1, 3 and 5 were derived from uninfected GBK cells (controls). Lanes 2, 4 and 6 were derived from GBK cells infected with PEH4-2 fusion protein. The lysates represented by lanes 1 and 2 were incubated with rabbit pre-immune sera. The lysates represented by lanes 3 and 4 were incubated with rabbit antiserum directed against the pEH4-2 fusion protein. The lysates represented by lanes 5 and 6 where incubated with monoclonal antibody 4S (a monoclonal antibody directed against gD). Lanes 4 and 6 clearly demonstrate that the 52,000 dalton gD protein produced by HSV-1 infected cells is immunoreactive with both the antisera directed against the fusion protein produced by pEH4-2 transformants and the 4S monoclonal antibody.

The above-described rabbit antisera directed against the fusion protein was also used to determine its ability to neutralize infection by HSV-1 in vitro. To this end, virus neutralization studies using a plaque assay were performed essentially as described by Showalter et al. (1981, *Infection and Immunity* 34: 684). Each dish (35 mm) of confluent GBK cells was infected with 50 p.f.u. (plaque forming units) of HSV-1 with control (pre-immune sera) or test antisera dilutions. After 3 days the cells were fixed and stained and plaques were counted. Table 1, below, shows the results of two such experiments. Neutralization is expressed as the serum dilution required to give a 50% reduction in plaque number. Table 1 clearly shows that the antisera directed against the pEH4-2 fusion protein is capable of neutralizing HSV-1 infection in vitro.

TABLE 1

Results of Neutralizaton Experiments

| Antibody | Neutralization* Expt 1 | Neutralization* Expt 2 |
|---|---|---|
| 4S monoclonal | 20,000+ | N.D. |
| Rabbit 018 | 200+ | 512 |
| Rabbit 019 | 200 | 256 |

*The numbers represent the antibody titer as that serum dilution which reduced plaque numbers by 50%. N.D. represents no data.

6.5 RECONSTRUCTION OF THE gD GENE

The plasmids pJS413 and pRWF6 were used to reconstruct the gD gene (FIG. 12).

Accordingly, pRWF6 was digested with Hind III and Bal 31 to generate a spectrum of randomly sized blunt-ended fragments. After digestion of these fragments with Sac I, the blunt-ended/Sac I fragments ranging from 2.2 to 2.4 kb were isolated. These fragments contained varying lengths of the amino-coding terminus of the gD gene (see FIG. 12).

The gD fragments were subcloned into pJS413. To this end, pJS413 was digested with Sma I (resulting in a blunt end) and Sac I (resulting in a Sac I 3'-cohesive end). The 4.7 kb Sma I/Sac I pJS413 fragment was ligated with the blunt-ended/Sac I pRWF6 fragment (2.2–2.4 Kb) in a 1:1 ratio and used to transform *E. coli* strain NF1829. This resulted in a population of clones transformed with plasmids which contained the gD gene randomly "deleted" at its amino-coding terminus (FIG. 12). In all, 24 plasmids, labeled pEH50+x (wherein x stands for 1 through 24), approximately 7 kb each, were analyzed by mapping the restriction enzyme recognition sites. Those which contained a Pvu II site within the gD gene (19 out of the 24 transformants) were further analyzed in order to identify the clone which contained the largest portion of the amino-coding terminus of gD.

In a complete gD gene sequence, the distance between the gD initiation ATG and the internal Pvu II site is 156 base pairs. Thus, each of the 19 pEH50+x plasmids was digested with Bgl II and Pvu II; the resulting fragments were resolved by gel electrophoresis in order to determine the size of the Bgl II/Pvu II fragment. Fifteen pEH50+x plasmids having a Bgl II/Pvu II fragment smaller than 160 base pairs were identified, i.e., the end point of the Bal 31 digestion depicted in FIG. 12 was somewhere between the gD initiation ATG and the Pvu II site. These fifteen were sequenced to precisely determine the site of ligation to the pJS413 plasmid. Seven plasmids, pEH51, pEH60, pEH62, pEH66, pEH71, pEH73 and pEH74, contained the gD sequence ligated in frame with the cro ATG of pJS413 (see FIG. 3 where these ligation sites are indicated by the corresponding pEH number and a vertical arrow). In fact, pEH51 encodes all but the first 6 amino acids of the gD amino-terminus.

Transformants of pEH51, pEH60, pEH62 and pEH71 were labeled with $^{35}$S-methionine with or without IPTG induction and cell lysates were treated with monoclonal antibody 55S; the immunoprecipitates were analyzed by SDS-PAGE as previously described. Transformants containing pEH51, pEH60, pEH62 or pEH71 each produced a 46,000 dalton inducible protein which precipitated with monoclonal 55S (data not shown).

Finally, recombinant plasmids which encode fusion proteins were made using the amino-coding terminus of pEH51 to reconstruct the amino-coding terminus of the gD gene sequence present in pEH4-2 (see FIG. 13). The plasmid pEH4-2 was digested with Pst I and Sac II and the 6.3 kb fragment containing the partial gD/β-galactosidase gene was isolated. The plasmid pEH51 was totally digested with Pst I, but partially digested with Sac II. The 1.25 kb Pst I/Sac II fragment of pEH51 was ligated in a 1:1 ratio with the 6.3 kb Pst I/Sac II fragment of pEH4-2 to form pEH82. Transformants were identified by screening for β-galactosidase activity as previously described. *E. coli* transformants bearing the pEH51 plasmid are designated *E. coli* strain WW51; those transformants bearing the pEH82 plasmid are designated *E. coli* strain WW82.

It is to be understood that all base pair sizes given for nucleotides are approximate and are used for purposes of description. Furthermore, it is apparent that many modifications and variations of this invention as hereinbefore set forth may be made without departing from the spirit and scope thereof. The specific embodiments described are given by way of example only and the invention is limited only by the appended claims.

An *E. coli* strain, K-12, MC1000, NF1829, carrying the pEH51 (*E. coli* WW51) or the pEH82 (*E. coli* WW82) plasmid described herein have been deposited with The American Type Culture Collection, Rockville, Md. and have been assigned accession numbers 39,159 and 39,160, respectively. An *E. coli* strain carrying plasmid pJS413 described herein has been deposited with the Agricultural Research Culture Collection (NRRL), Peoria, Ill., and has been assigned accession number B-15237. A culture of the deposited microorganisms will be made available to the public upon the grant of patent based upon the present application. It is to be understood that the availability of a deposit does not constitute a license to practice the subject invention in derogation of patent rights granted by the United States government. Furthermore, the present invention is not to be limited in scope by the microorganism deposited, since the deposited embodiment is intended as a single illustration of one aspect of the invention. Indeed, various modifications of the invention in addition to those shown and described herein will become apparent to those skilled in the art from the foregoing description and accompanying drawings. Such modifications are intended to fall within the scope of the appended claims.

We claim:

1. A process for producing a polypeptide comprising the amino acid sequence of a Herpes Simplex Virus qD glycoprotein or a fragment of said amino acid sequence, wherein said fragment comprises at lest seven contiguous amino acids, said polypeptide containing at least one immunological and antigenic determinant of a Herpes Simplex Virus gD glycoprotein comprising:

(a) culturing a unicellular organism containing a recombinant vector comprising a DNA sequence coding for a polypeptide comprising the amino acid sequence of a Herpes Simplex Virus gD glycoprotein or a fragment of said amino acid seqeunce, wherein said fragment comprises at least seven contiguous amino acids, said polypeptide containing at least one immunological and antigenic determinant of a Herpes Simplex Virus gD glycoprotein, and said recombinant vector capable of being replicated in said unicellular organism and said unicellular organism capable of producing said polypeptide; and (b) isolating said polypeptide from the culture.

2. The process according to claim 1, wherein the recombinant vector was introduced into the unicellular organism by transformation.

3. The process according to claim 1, wherein the recombinant vector was introducel into the unicellular organism by transduction.

4. The process according to claim 1, wherein the recombinant vector was introduced into the unicellular organism by transfection.

5. The process according to claim 1, wherein the information contained in the DNA sequence was obtained from a Herpes Simplex Virus genome.

6. The process according to claim 5, wherein the information contained in the DNA sequence was obtained from Herpes Simplex Virus type 1.

7. The process according to claim 1, wherein the information contained in the DNA sequence was obtained by isolating mRNA coding for a Herpes Simplex Virus gD glycoprotein and using reverse transcriptase to construct said DNA sequence having one strand complementary to the isolated mRNA.

8. The process according to claim 1, wherein the DNA sequence was obtained from a DNA vector containing a Herpes Simplex virus DNA sequence.

9. The process according to claim 1, wherein the DNA sequence codes for the gD glycoprotein of Herpes Simplex Virus type 1.

10. The process according to claim 1, wherein the unicellular organism is a eucaryotic organism.

11. The process according to claim 1, wherein the unicellular organism is a procaryotic organism.

12. The process according to claim 11, wherein the procaryotic organism is *Escherichia coli*.

13. The process according to claim 12, wherein the *Escherichia coli* has ATCC accession No. 39,159.

14. The process according to claim 12, wherein the *Escherichia coli* has ATCC accession No. 39,160.

15. A process for preparing a unicellular organism having a DNA sequence coding for a polypeptide comprising the amino acid sequence of a Herpes Simplex Virus gD glycoprotein or a fragment of said amino acid sequence, wherein said fragment comprises at least seven contiguous amino acids, said polypeptide containing at least one immunolgocial and antigenic determinant of a Herpes Simplex Virus gD glycoprotein, comprising: introducing a recombinant vector into a unicellar orgainism, said recombinant vector comprising a DNA sequence coding for a polypeptide comprising the amino acid sequence of a Herpes Simplex Virus gD glycoprotein or a fragment of said amino acid sequence, wherein said fragment comprises at least seven contiguous amino acids, said polypeptide containing at least one immunological and antigenic determinant of a Herpes Simplex Virus gD glycoprotein, and said recombinant vector capable of being replicated in said unicellar organism and said unicellar organism capable of producing said polypeptide.

16. The process of claim 17, wherein the Herpes Simplex Virus is Herpes Simplex Virus Type 1.

17. The process of claim 15, wherein at least one determinant is common to Herpes Simplex Virus Type 1 and Type 2.

18. A purified DNA sequence coding for a polypeptide comprising the amino acid sequence of a Herpes Simplex virus gD glycoprotein or a fragment of said amino acid sequence, wherein said fragment comprises at least seven contiguous amino acids, said polypeptide containing at least one immunological and antigenic determinant of a Herpes Simplex Virus gD glycoprotein, in which such DNA sequence is free of Herpes Simplex Virus-coded translation stop signals in phase and 5', to the triplet signal coding for the first amino acid of said polypeptide.

19. The purified DNA sequence of claim 18, in which the determinnat is specific to Herpes Simplex Virus Type 1.

20. The purified DNA sequence of claim 18, in which the determinant is common to Herpes Simplex Virus Type 1 and Type 2.

21. The purified DNA sequence of claim 18, in which the sequence comprises GGG GGG ACT GCC GCC AGG TTG GGG GCC GTG ATT TTG TTT GTC GTC ATA GTG GGC CTC CAT GGG GTC CGC GGC AAA TAT GCC TTTG GCG GAT GCC TCT CTC AAG ATG GCC GAC CCC AAT CGC TTT CGC GGC AAA GAC CTT CCG GTC CTG GAC CAG CTG ACC GAC CCT CCG GGG GTC CGG CGC GTG TAC CAC ATC CAG GCG CGC CTA CCG GAC CCG TTC CAG CCC CCC AGC CTC CCG ATC ACG GTT TAC TAC GCC GTG TTG GAG CGC GCC TGC CGC AGC CTC CTC CTA AAC GCA CCG TCG GAG GCG CCC CAG ATT GTC CGC GGG GCC TCC GAA GAC GTC CGG AAA CAA CCC TAC AAC CTG ACC ATC GCT TGG TTT CGG ATG GGA GGC AAC TGT GCT ATC CCC ATC ACG GTC ACG GAG TAC ACC GAA TGC TCC TAC AAC AAG TCT CTG GGG GCC TGT CCC ATC CGA ACG CAG CCC CGC TGG AAC TAC TAT GAC AGC TTC AGC GCC GTC AGC GAG GAT AAC CTG GGG TTC CTG ATG CAC GCC CCC GCG TTT GAG ACC GCC GGC ACG TAC CTG CGG CTC GTG AAG ATA AAC GAC TGG ACG GAG ATT ACA CAG TTT ATC CTG GAG CAC CGA GCC AAG GGC TCC TGT AAG TAC GCC CTC CCG CTG CGC ATC CCC CCG TCA GCC TGC CTC TCC CCC CAG GCC TAC CAG CAG GGG GTG ACG GTG GAC AGC ATC GGG ATG CTG CCC CGC TTC ATC CCC GAG AAC CAG CGC ACC GTC GCC GTA TAC AGC TTG AAG ATC GCC GGG TGG CAC GGG CCC AAG GCC CCA TAC ACG AGC ACC CTG CTG CCC CCG GAG CTG TCC GAG ACC CCC AAC GCC ACG CAG CCA GAA CTC GCC CCG GAA GAC CCC GAG GAT TCG GCC CTC TTG GAG GAC CCC GTG GGG ACG GTG GCG CCG CAA ATC CCA CCA AAC TGG CAC ATC CCG TCG ATC CAG GAC GCG ACG CCT TAC CAT CCC CCG GCC ACC CCG AAC AAC ATG GGG CTG ATC GCC GGC GCG GTG GGC GGC AGT CTC CTG GCA GCC CTG GTC ATT TGC GGA ATT GTG TAC TGG ATG CAC CGC CGC ACT CGG AAA GCC CCA AAG CGC ATA CGC CTC CCC CAC ATC CGG GAA GAC GAC CAG CCG TCC TCG CAC CAG CCC TTG TTT TAC, or a subsequence thereof, which subsequence comprises at least 21 contiguous nucleotides of said sequence and codes on expression for a polypeptide having at least one immunological and antigenic determinant of a Herpes Simplex virus gD glycoprotein.

22. A unicellular organism containing an exogenous DNA sequence coding for a polypeptide comprising the amino acid sequence of a Herpes Simplex Virus gD glycoprotein or a fragment of said amino acid sequence, wherein said fragment comprises at least seven contiguous amino acids, said polypeptide containing at least one immunological and antigenic determinant of a Herpes Simplex Virus gD glycoprotein, wherein the unicellular orgainism is capable of expressing the DNA sequence to produce said polypeptide.

23. A unicellular organism containing a recombinant vector comprising a DNA sequence coding for polypeptide comprsiing the amino acid sequence of a Herpes Simplex Virus gD glycoprotein or a fragment of said amino acid sequence, wherein said fragment comprises at least seven contiguous amino acids, said polypeptide containing at least one immunological and antigeninc determinant of a Herpes Simplex Virus gD glycoprotein, wherein said recombinant vector is capable of being replicated in said unicellular organism and said unicellular orgainism is capable of expressing the DNA sequence to produce said polypeptide.

24. The unicellular organism of claim 22 or 23, wherein the Herpes Simplex Virus is Herpes Simplex Virus Type 1.

25. The unicellular organism of claim 22 or 23, wherein at least one determinanat is common to Herpes Simplex Virus Type 1 and Type 2.

26. The unicellular organism of claim 22 or 23, wherein the unicellular organism is a yeast.

27. The unicellar organism of claim 24, wherein the unicellar organism is a yeast.

28. The unicellular organism of claim 25, wherein the unicellular organism is a yeast.

29. The unicellular organism of claim 23, in which the DNA sequence in such recombinant vector is under the control of a transcription promoter and translation initiation signal.

30. The unicellular organism of claim 23, in which such recombinant vector further comprises the PBR322 replication origin.

31. The unicellar organism of claim 23, in which the DNA seqeunce in such recombinant vector is connected in phase to a second DNA sequence coding for a protein.

32. A recombinant vector comprising (a) a DNA sequence coding for a polypeptide comprising the amino acid sequence of a Herpes Simplex Virus gD glycoprotein or a fragment of said amino acid sequence, wherein said fragment comprises at least seven contiguous amino acids, said polypeptide containing at least one immunological and antigenic determinant of a Herpes Simplex Virus gD glycoprotein and (b) DNA from a vector derived from a plasmid, virus or cell which does not exchange genetic information with Herpes Simplex Virus in nature, wherien the recombinant vector is capable of being replicated in a compatible host cell and capable of directing expression of the DNA sequence in said host cell to produce said polypeptide.

33. The recombinant vector of claim 32, further comprising the PBR322 replication origin.

34. The recombinant vector of claim 32, in which the DNA sequence is connected in phase to a second DNA sequence coding for a protein.

35. The recombinant vector of claim 32, wherein the Herpes Simplex Virus is Herpes Simplex Virus Type 1.

36. The recombinant vector of claim 32, wherein at least one determinant is common to Herpes Simplex Virus Type 1 and Type 2.

37. A eucaryotic cell containing an exgenous DNA sequence coding for a polypeptide comprising the amino acid sequence of a Herpes Simplex Virus gD glycoprotein or a fragment of said amino acid sequence, wherein said fragment comprises at least seven contiguous amino acids, said polypeptide containing at least one immunological and antigenic determinant of a Herpes Simplex Virus gD glycoprotein, wherein the eucaryotic cell is capable of expressing the DNA sequence to produce said polypeptide and does not contain the entirety of the Herpes Simplex Virus genetic information.

38. A eucaryotic cell containin an exogenous DNa sequence coding for a polypeptide comprising the amino acid sequence of a Herpes Simplex Virus gD glycoprotein or a fragement of said amino acid sequence, wherein said fragment comprises at least seven contiguous amino acids, said polypeptide containing at least one immunological and antigenic determinant of a herpes Simplex Virus gD glycoprotein, wherein the eucaryotic cell is capable of expressing the DNA sequence to produce said polypeptide and is not a natural host for Herpes Simplex Virus.

39. The eucaryotic cell of claim 37 or 38, wherein the Herpes Simplex Virus is Herpes Simplex Virus Type 1.

40. The eucaryotic cell of claim 37 or 38, wherein at least one determinant is common to Herpes Simplex Virus Type 1 and Type 2.

41. The recombinant vector pEH51.

42. The recombinant vector pEH82.

43. A unicellular organism containing the recombinant vector pEH51.

44. A procarbyotic cell containing an exogenous DNA sequence coding for a polypeptide comprising the amino acid sequence of a Herpes Simplex Virus gD glycoprotein or a fragment of said amino acid sequence, wherein said fragment comprises at least seven contiguous amino acids, said polypeptide containing at least one immunological and antigenic determinant of a Herpes Simplex Virus gD glycoprotein, wherein the procaryotic cell is capable of expressing the DNA sequence to produce said polypeptide.

45. The process of claim 1, wherein said unicellular organism is a yeast.

46. A unicellular organism containing the exogenous DNA sequence: GGG GGG ACT GCC GCC AGG TTG GGG GCC GTG ATT TTG TTT GTC GTC ATA GTG GGC CTC CAT GGG GTC CGC GGC AAA TAT GCC TTG GCG GAT GCC TCT CTC AAG ATG GCC GAC CCC AAT CGC TTT CGC GGC AAA GAC CTT CCG GTC CTG GAC CAG CTG ACC GAC CCT CCG GGG GTC CGG CGC GTG TAC CAC ATC CAG GCG GGC CTA CCG GAC CCG TTC CAG CCC CCC AGC CTC CCG ATC ACG GTT TAC TAC GCC GTG TTG GAG CGC GCC TGC CGC AGC GTG CTC CTA AAC GCA CCG TCG GAG GCG CCC CAG ATT GTC CGC GGG GCC TCC GAA GAC GTC CGG AAA CAA CCC TAC AAC CTG ACC ATC GCT TGG TTT CGG ATG GGA GGC AAC TGT GCT ATC CCC ATC ACG GTC ACG GAG TAC ACC GAA TGC TCC TAC AAC AAG TCT CTG GGG GCC TGT CCC ATC CGA ACG CAG CCC CGC TGG AAC TAC TAT GAC AGC TTC AGC GCC GTC AGC GAG GAT AAC CTG GGG TTC CTG ATG CAC GCC CCC GCG TTT GAG ACC GCC GGC ACG TAC CTG CGG CTC GTG AAG ATA AAC GAC TGG ACG GAG ATT ACA CAG TTT ATC CTG GAG CAC CGA GCC AAG GGC TCC TGT AAG TAC GCC CTC CCG CTG CGC ATC CCC CCG TCA GCC TGC CTC TCC CCC CAG GCC TAC CAG CAG GGG GTG ACG GTG GAC AGC ATC GGG ATG CTG CCC CGC TTC ATC CCC GAG AAC CAG CGC ACC GTC GCC GTA TAC AGC TTG AAG ATC GCC GGG TGG CAC GGG CCC AAG GCC CCA TAC ACG AGC ACC CTG CTG CCC CCG GAG CTG TCC GAG ACC CCC AAC GCC ACG CAG CCA GAA CTC GCC CCG GAA GAC CCC GAG GAT TCG GCC CTC TTG GAG GAC CCC GTG GGG ACG GTG GCG CCG CAA ATC CCA CCA AAC TGG CAC ATC CCG TCG ATC CAG GAC GCC GCG ACG CCT TAC CAT CCC CCG GCC ACC CCG AAC AAC ATG GGG CTG ATC GCC GGC CGG GTG GGC GGC AGT CTC CTG GCA GCC CTG GTC ATT TGC GGA ATT GTG TAC TGG ATG CAC CGC CGC ACT CGG AAA GCC CCA AAG CGC ATA CGC CTC CCC CAC ATC CGG GAA GAC GAC CAG CCG TCC TCG CAC CAG CCC TTG TTT TAC, or a subsequence thereof, which subsequence comprises at least 21 continguous nucleotides of said sequence and codes on expression for a polypeptide having at least one immunological and antigenic determinant of a Herpoes Simplex Virus gD glycoprotein, wherein said polypeptide comprises at least seven contiguous amino acids and said unicellular organism is capable of expressing the DNA sequence to produce said polypeptide.

47. A recombinant vector comprising the DNA sequennce: GGG GGG ACT GCC GCC AGG TTG GGG GCC GTG ATT TTG TTT GTC GTC ATA GTG GGC CTC CAT GGG GTC CGC GGC AAA TAT GCC TTG GCG GAT GCC TCT CTC AAG ATG GCC GAC CCC AAT CGC TTT CGC GGC AAA GAC CTT CCG GTG CTG GAC CAG CTG ACC GAC CCT CCG GGG GTC CGG CGC GTG TAC CAC ATC CAG GCG GGC CTA CCG GAC CCG TTC CAG CCC CCC AGC CTC CCG ATC ACG GTT TAC TAC GCC GTG TTG GAG CGC GCC TGC CGC AGC GTG CTC CTA AAC GCA CCG TCG GAG GCG CCC CAG ATT GTC CGC GGG GCC TCC GAA GAC GTC CGG AAA CAA CCC TAC AAC CTG ACC ATC GCT TGG TTT CGG ATG GGA GGC AAC TGT GCT ATC CCC ATC ACG GTC ACG GAG TAC ACC GAA TGC TCC TAC AAC AAG TCT CTG GGG GCC TGT CCC ATC CGA ACG CAG CCC CGC TGG AAC TAC TAT GAC AGC TTC AGC GCC GTC AGC GAG GAT AAC CTG GGG TTC CTG ATG CAC GCC CCC GCG TTT GAG ACC GCC GGC ACG TAC CTG CGG CTC GTG AAG ATA AAC GAC TGG ACG GAG ATT ACA CAG TTT ATC CTG GAG CAC CGA GCC AAG GGC TCC TGT AAG TAC GCC CTC CCG CTG CGC ATC CCC CCG TCA GCC TGC CTC TCC CCC CAG GCC TAC CAG CAG GGG GTG ACG GTG GAC AGC ATC GGG ATG CTG CCC CGC TTC ATC CCC GAG AAC CAG CGC ACC GTC GCC GTA TAC AGC TTG AAG ATC GCC GGG TGG CAC GGG CCC AAG GCC CCA TAC ACG AGC ACC CTG CTG CCC CCG GAG CTG TCC GAG ACC CCC AAC GCC ACG CAG CCA GAA CTC GCC CCG GAA GAC CCC GAG GAT TCG GCC CTC TTG GAG GAC CCC GTG GGG ACG GTG GCG CCG CAA ATC CCA CCA AAC TGG CAC ATC CCG TCG ATC CAG GAC GCC GCG ACG CCT TAC CAT CCC CCG GCC ACC CCG AAC AAC ATG GGG CTG ATC GCC GGC GCG GTG GGC GGC AGT CTC CTG GCA GCC CTG GTC ATT TGC GGA ATT GTG TAC TGG ATG CAC CGC CGC ACT CGG AAA GCC CCA AAG CGC ATA CGC CTC CCC CAC ATC CGG GAA GAC GAC CAG CCG TCC TCG CAC CAG CCC TTG TTT TAC, or a subsequence thereof which subsequence comprises at least 21 contiguous nucleotide of said sequence and codes on expression for a polypeptide having at least one immunological and natigenic determinant of a Herpes Simplex Virus gD glycoprotein, wherein said polypeptide comprises at least seven contiguous amino acids and said recombinant vector is capable of being replicated in a compatible host cell and capable of directing expression of the DNA sequence in said host cell to produce said polypeptide.

48. The recombinant vector of claim 47, wherein said DNA sequence is under the control of a transcription promoter and at translation initiation signal.

49. The recombinant vector of claim 47, further comprising the pBR322 replication origin.

50. The recombinant vector of claim 47, wherein said DNA sequence is connected in phases to a second DNA sequence coding for a protein.

51. A unicellular organism containing a recombinanat vector comprising the DNA sequence: GGG GGG ACT GCC GCC AGG TTG GGG GCC GTG ATT TTG TTT GTC GTC ATA GTG GGC CTC CAT GGG GTC CGC GGC AAA TAT GCC TTG GCG GAT GCC TCT CTC AAG ATG GCC GAC CCC AAT CGC TTT CGC GGC AAA GAC CTT CCG GTC CTG GAC CAG CTG ACC GAC CCT CCG GGG GTC CGG CGC GTG TAC CAC ATC CAG GCG GGC CTA CCG GAC CCG TTC CAG CCC CCC AGC CTC CCG ATC ACG GTT TAC TAC GCC GTG TTG GAG CGC GCC TGC CGC AGC GTG CTC CTA AAC GCA CCG TCG GAG GCG CCC CAG ATT GTC CGC GGG GCC TCC GAA GAC GTC CGG AAA CAA CCC TAC ACC CTG ACC ATC GCT TGG TTT CGG ATG GGA GGC AAC TGT GCT ATC CCC ATC ACG GTC ACG GAG TAC ACC GAA TGC TCC TAC AAC AAG TCT CTG GGG GCC TGT CCC ATC CGA ACG CAG CCC CGC TGG AAC TAC TAT GAC AGC TTC AGC GCC GTC AGC GAG GAT AAC CTG GGG TTC CTG ATG CAC GCC CCC GCG TTT GAG ACC GCC GGC ACG TAC CTG CGG CTC GTG AAG ATA AAC GAC TGG ACG GAG ATT ACA CAG TTT ATC CTG GAG CAC CGA GCC AAG GGC TCC TGT AAG TAC GCC CTC CCG CTG CGC ATC CCC CCG TCA GCC TGC CTC TCC CCC CAG GCC TAC CAG CAG GGG GTG ACG GTG GAC AGC ATC GGG ATG CTG CCC CGC TTC ATC CCC GAG AAC CAG CGC ACC GTC GCC GTA TAC AGC TTG AAG ATC GCC GGG TGG CAC GGG CCC AAG GCC CCA TAC ACG AGC ACC CTG CTG CCC CCG GAG CTG TCC GAG ACC CCC AAC GCC ACG CAG CCA GAA CTC GCC CCG GAA GAC CCC GAG GAT TCG GCC CTC TTG GAG GAC CCC GTG GGG ACG GTG CCG CCG CAA ATC CCA CCA AAC TGG CAC ATC CCG TCG ATC CAG GAC GCC GCG ACG CCT TAC CAT CCC CCG GCC ACC CCG AAC AAC ATG GGG CTG ATC GCC GGC GCG GTG GGC GGC AGT CTC CTG GCA GCC CTC GTC ATT TGC GGA ATT GTG TAC TGG ATG CAC CGC CGC ACT CGG AAA GCC CCA AAG CGC ATA CGC CTC CCC CAC ATC CGG GAA GAC GAC CAG CCG TCC TCG CAC CAG CCC TTG TTT TAC, or a subsequence thereof, which subsequence comprises at least 21 contiguous nuleotides of said sequence and codes on expression for a polypeptide having at least one immunological and antigenic determinant of a Herpes Simplex Virus gD glycoprotein, wherein said polypeptide comprises at least seven contiguous amino acids and said recombinant vector is capable of being replicated in said unicellular organism and said unicellular orgainsim is capable of expressing the DNA sequence to produce said polypeptide.

52. The unicellular organism of claim 51, wherein said DNA sequence is under the control of a transcription promoter and a translation initiation signal.

53. The unicellular organism of claim 51, wherein said recombinant vector comprises the pBR322 replication origin.

54. The unicellular organism of claim 51, wherein said DNA sequence is connected in phase to a second DNA sequence coding for a protein.

55. An *Escherichia coli* bacterium as deposited with the ATCC and assigned accession No. 39,159.

56. An *Escherichia coli* bacterium as deposited with the ATCC and assigned aaccession No. 39,160.

57. An *Escherichia coli* bacterium containing the exogenous DNA sequence: GGG GGG ACT GCC GCC AGG TTG GGG GCC GTG ATT TTG TTT GTC GTC ATA GTG GGC CTC CAT GGG GTC CGC GGC AAA TAT GCC TTG GCG GAT GCC TCT CTC AAG ATG GCC GAC CCC AAT CGC TTT CGC GGC AAA GAC CTT CCG GTC CTG GAC CAG CTG ACC GAC CCT CCG GGG GTC CGG CGC GTG TAC CAC ATC CAG GCG GGC CTA CCG GAC CCG TTC CAG CCC CCC AGC CTC CCG ATC ACG GTT TAC TAC GCC GTG TTG GAG CGC GCC TGC CGC AGC GTG CTC CTA AAC GCA CCG TCG GAG GCG CCC CAG ATT GTC CGC GGG GCC TCC GAA GAC GTC CGG AAA CAA CCC TAC AAC CTG ACC ATC GCT TGG TTT CGG ATG GGA GGC AAC TGT GCT ATC CCC ATC ACG GTC ACG GAG TAC ACC GAA TGC TCC TAC AAC AAG TCT CTG GGG GCC TGT CCC ATC CGA ACG CAG CCC CGC TGG AAC TAC TAT GAC AGC TTC AGC GCC GTC AGC GAG GAT AAC CTG GGG TTC CTG ATG CAC GCC CCC GCG TTT GAG ACC GCC GGC ACG TAC CTG CGG CTC GTC AAG ATA AAC GAC TGG ACG GAG ATT ACA CAG TTT ATC CTG GAG CAC CGA GCC AAG GGC TCC TGT AAG TAC GCC CTC CCG CTG CGC ATC CCC CCG TCA GCC TGC CTC TCC CCC CAG GCC TAC CAG CAG GGG GTG ACG GTG GAC AGC ATC GGG ATG CTG CCC CGC TTC ATC CCC GAG AAC CAG CGC ACC GTC GCC GTA TAC AGC TTG AAG ATC GCC GGG TGG CAC GGG CCC AAG GCC CCA TAC ACG AGC ACC CTG CTG CCC CCG GAG CTG TCC GAG ACC CCC AAC GCC ACG CAG CCA GAA CTC GCC CCG GAA GAC CCC GAG GAT TCG GCC CTC TTG GAG GAC CCC GTG GGG ACG GTG GCG CCG CAA ATC CCA CCA AAC TGG CAC ATC CCG TCG ATC CAG GAC GCC GCG ACG CCT TAC CAT CCC CCG GCC ACC CCG AAC AAC ATG GGG CTG ATC GCC GGC GCG GTG GGC GGC AGT CTC CTG GCA GCC CTG GTC ATT TGC GGA ATT GTG TAC TGG ATG CAC CGC CGC ACT CGG AAA GCC CCA AAG CGC ATA CGC CTC CCC CAC ATC CGG GAA GAC GAC CAG CCG TCC TCG CAC CAG CCC TTG TTT TAC, or a subsequence thereof, which subsequence comprises at least 21 contiguous nucleotides of said sequence and codes on expression for a polypeptide having at least one immunological and antigenic determinant of a Herpes Simplex Virus gD glycoprotein, wherein said polypeptide comprises at least seven contiguous amino acids and said bacterium is capable of expressing the DNA sequence to produce said polypeptide.

58. An *Escherichia coli* bacterium containing an exogenous DNA sequence coding for a polypeptide comprising the amino acid sequence of a Herpes Simplex Virus gD glycoprotein or a fragment of said amino acid sequence, wherein said fragment comprises at least seven contignuous amino acids, said polypeptide containing at least one immunological and antigenic determinanat of a Herpes Simplex Virus gD glycoprotein, and wherein the bacterium is capable of expressing the DNa sequence to produce said polypeptide.

59. An *Escherichia coli* bacterium containing a recombinant vector comprising a DNA sequence coding for a polypeptide comprising the amino acid sequence of a Herpes Simplex Virus gD glycoprotein or a fragement of said amino acid sequence, wherein said fragment comprises at least seven contiguous amino acids, said polypeptide containing at least one immunolgocal and antigenic determinanat of a herpes Simplex Virus gD glycoprotein, in which such DNa sequence is connected in phase to a second DNA sequence coding for a protein, and the recombinant vector is capable of being replicated in said bacterium and said bacterium is capable of expressing the DNA sequence to produce said polypeptide.

60. The bacterium of claim 58 or 59, wherein the Herpes Simplex Virus is Herpes Simplex Virus Type 1.

61. The bacterium of claim 58 or 59, wherein at least one determinant is common to Herpes Simplex Virus Type 1 and Type 2.

* * * * *